US009610092B2

(12) United States Patent
Penenberg

(10) Patent No.: US 9,610,092 B2
(45) Date of Patent: *Apr. 4, 2017

(54) PRECISION HIP REPLACEMENT METHOD

(75) Inventor: Brad L. Penenberg, Los Angeles, CA (US)

(73) Assignee: Microsoft Orthopedics Holdings Inc., Tiel (NL)

( * ) Notice: Subject to any disclaimer, the term of this patent is extended or adjusted under 35 U.S.C. 154(b) by 1199 days.

This patent is subject to a terminal disclaimer.

(21) Appl. No.: 13/431,944

(22) Filed: Mar. 27, 2012

(65) Prior Publication Data

US 2013/0053856 A1 Feb. 28, 2013

Related U.S. Application Data

(60) Provisional application No. 61/528,744, filed on Aug. 29, 2011, provisional application No. 61/567,869, filed on Dec. 7, 2011.

(51) Int. Cl.

| A61B 17/58 | (2006.01) |
|---|---|
| A61B 17/60 | (2006.01) |
| A61F 2/00 | (2006.01) |
| A61B 17/3209 | (2006.01) |
| A61F 2/46 | (2006.01) |
| A61B 17/17 | (2006.01) |

(Continued)

(52) U.S. Cl.
CPC .... *A61B 17/32093* (2013.01); *A61B 17/1703* (2013.01); *A61B 17/320016* (2013.01); *A61F 2/4609* (2013.01); *A61B 17/164* (2013.01); *A61B 17/1659* (2013.01); *A61B 17/1668* (2013.01); *A61B 17/175* (2013.01); *A61B 17/1746* (2013.01); *A61B 2017/320044* (2013.01)

(58) Field of Classification Search
CPC ... A61F 2/4609; A61F 2/34; A61F 2002/4623
USPC ............................................... 606/91
See application file for complete search history.

(56) References Cited

U.S. PATENT DOCUMENTS

| 4,808,185 A | 2/1989 | Penenberg |
| 5,788,705 A | 8/1998 | Huddleston et al. |

(Continued)

FOREIGN PATENT DOCUMENTS

| WO | WO 2010/030809 | 3/2010 |
| WO | WO 2010/031111 | 3/2010 |

*Primary Examiner* — David Isabella
*Assistant Examiner* — Christine Nelson
(74) *Attorney, Agent, or Firm* — Adams and Reese LLP

(57) ABSTRACT

A method for accurately positioning the acetabular cup in a minimally invasive total hip arthroplasty (THA), comprising the steps of (a) placing the cup in roughly the correct position in the acetabulum using a acetabular component placement tool, (b) taking a first abduction reading and a first anteversion reading using a gyroscopic positioning unit aligned with the acetabular component placement tool, (c) taking an image of at least a portion of the cup using a radiography unit, (d) using the image to determine the actual orientation of the cup and required position of the cup to properly orient the acetabular component, (e) incrementally altering the position of the cup by using a striking tool, (f) taking new abduction and anteversion readings using the gyroscopic unit to determine the relative movement of the cup caused by the tapping, and (g) repeating any of the steps as necessary.

10 Claims, 15 Drawing Sheets

(51) Int. Cl.
*A61B 17/32* (2006.01)
*A61B 17/16* (2006.01)

(56) References Cited

U.S. PATENT DOCUMENTS

| | | |
|---|---|---|
| 5,910,172 A | 6/1999 | Penenberg |
| 5,989,259 A | 11/1999 | Penenberg |
| 6,007,483 A * | 12/1999 | Kieturakis ......... A61B 17/0218 600/115 |
| 6,589,285 B2 | 7/2003 | Penenberg |
| 6,697,664 B2 | 2/2004 | Kienzle, III et al. |
| 6,905,502 B2 | 6/2005 | Penenberg |
| 6,997,928 B1 | 2/2006 | Penenberg |
| D553,751 S | 10/2007 | Penenberg |
| 7,396,328 B2 | 7/2008 | Penenberg |
| 7,582,090 B2 | 9/2009 | Penenberg |
| 7,651,501 B2 | 1/2010 | Penenberg |
| 7,660,624 B2 | 2/2010 | Georg et al. |
| 7,702,379 B2 | 4/2010 | Avinash et al. |
| 7,819,879 B2 | 10/2010 | Penenberg |
| 7,833,229 B2 | 11/2010 | Penenberg |
| 8,034,057 B2 | 10/2011 | Penenberg |
| 8,439,928 B2 | 5/2013 | Penenberg |
| 8,740,907 B2 | 6/2014 | Penenberg |
| 8,831,324 B2 | 9/2014 | Penenberg |
| 2003/0229352 A1 | 12/2003 | Penenberg |
| 2004/0181149 A1 | 9/2004 | Langlotz et al. |
| 2005/0149050 A1 | 7/2005 | Stifter et al. |
| 2005/0209604 A1 * | 9/2005 | Penenberg ............. A61B 17/92 606/91 |
| 2006/0217737 A1 | 9/2006 | Iverson |
| 2007/0233151 A1 * | 10/2007 | Chudik ............... A61B 17/1764 606/96 |
| 2009/0099570 A1 | 4/2009 | Paradis et al. |
| 2009/0099665 A1 | 4/2009 | Taylor et al. |
| 2009/0138019 A1 | 5/2009 | Wasielewski |
| 2010/0076505 A1 | 3/2010 | Borja |
| 2011/0015642 A1 | 1/2011 | Penenberg |
| 2012/0116412 A1 | 5/2012 | Penenberg |
| 2013/0053857 A1 | 2/2013 | Penenberg |
| 2013/0053858 A1 | 2/2013 | Penenberg |
| 2013/0053859 A1 | 2/2013 | Penenberg |
| 2013/0053904 A1 | 2/2013 | Penenberg |
| 2013/0190770 A1 | 7/2013 | Penenberg |
| 2014/0378828 A1 | 12/2014 | Penenberg |
| 2015/0150585 A1 | 6/2015 | Penenberg |

* cited by examiner

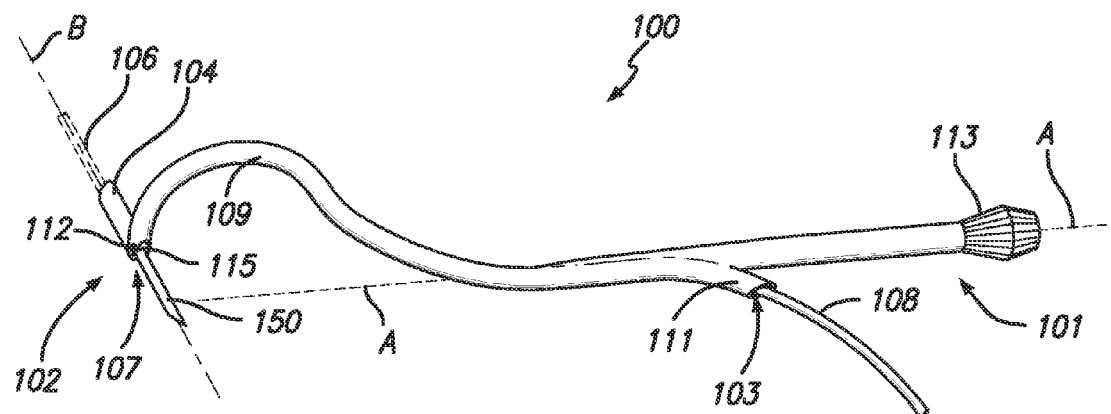
FIG. 2A
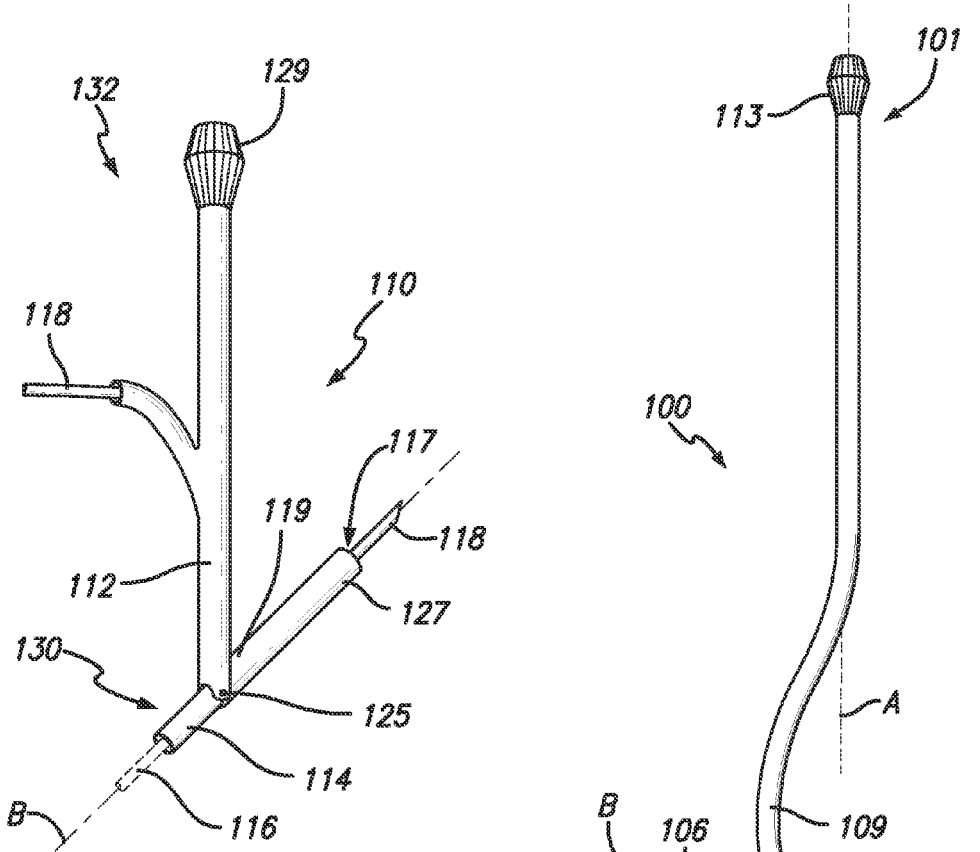
FIG. 2B
FIG. 2C

PRECISION HIP REPLACEMENT METHOD

CROSS-REFERENCES TO RELATED APPLICATIONS

This patent application claims the benefit of U.S. Provisional Application No. 61/528,744, filed Aug. 29, 2011, and U.S. Provisional Patent Application No. 61/567,869, filed Dec. 7, 2011. All applications are incorporated herein by this reference thereto.

BACKGROUND OF THE INVENTION

Field of the Invention

This invention relates to the field of minimally invasive surgical techniques for a joint replacement, and more particularly, methods for accurately positioning components for hip or knee joint replacement procedures.

Description of the Related Art

During the course of total hip arthroplasty, acetabular and femoral prostheses are placed. In order for the implants to function up to their capacity, generally meaning greater than twenty (20) years of clinical reliability, each component must be placed in a specific position in relation to the patient's native anatomy. Specifically, proper positioning of the acetabular component in a hip replacement procedure appears to be crucial to the long-term success of the surgery. What exactly constitutes proper positioning of the acetabular component is the subject of much debate. A commonly used range, established by Lewinnek et al., involves a cup position in which the abduction angle is within the range of 30° to 50° and in which the anteversion angle is within the range of 5° to 25°. Generally, surgeons use radiographic techniques to achieve these angles.

Studies have shown, however, that a substantially large percentage of surgeries result in cups that are not within this range. This is especially true with respect to minimally invasive surgical procedures. Callanan et al. surveyed 1952 hip replacements, observing several prediction factors, and found that only 48.7% resulted in acetabular cups within this range. Indeed, of the 93 hip replacements in Callanan's survey that used minimally invasive techniques, only 19.4% resulted in acetabular cups within this range.

This supports the proposition that traditional techniques have been considered by many to be unreliable for determining proper positioning of the acetabular cup or femoral component.

A variety of tools are available, however, to assist the surgeon in achieving correct component alignment. The so-called traditional guides, or line-of-sight, have been in use for over 40 years and are very helpful, but not as reliable as one would hope.

In the last 8-9 years, in an effort to improve reliability, there have been attempts at using so-called navigation or computer guidance systems relying on pre-operative CT scans to pre-load information pertaining to the patient's anatomy, intraoperative registration (a cumbersome and potentially tedious method to match the patient's anatomy to the preloaded image), the placement of multiple skeletal pins for orientation, and elaborate line-of-site transmitters relying on complex computer algorithms to guide component placement. Unfortunately, in spite of the promise of improved results, the reluctance of patients to be exposed to a significant amount of radiation during a CT scan, the significant cost of such a test against a simple intraoperative x-ray treatment, the total cost of the computer guidance system (many hundreds of thousands of dollars plus the ongoing cost of support annually as the machine is maintained and updated), the incalculable cost to the healthcare system, and the patient of an unpredictable workflow as system breakdown occurs frequently, add operation time and potential risk to the patient, as well as considerable cost. Consequently, this method has not been widely adopted.

Furthermore, in spite of the existence of such tools, the current success rate for acetabular component positioning is only sixty percent (60%). Therefore, there is still a need to improve the reliability and efficiency of instrumentation in achieving these specific recognized optimal component positions.

SUMMARY OF THE INVENTION

One embodiment of the present invention comprises methods for accurately positioning the acetabular cup in a minimally invasive, or conventional, total hip arthroplasty (THA), comprising the use of an elongated handle to place the cup in roughly the correct position with respect to the acetabulum of the patient, taking a first abduction reading and a first anteversion reading using a gyroscopic positioning unit aligned with the handle, taking an image of at least a portion of the cup using a radiography unit, using the image to determine the actual orientation of the cup and thereby the amount of movement in the abduction plane and in the anteversion plane to properly orient the acetabular component, incrementally altering the position of the cup by using a striking tool and an elongated instrument to tap a contact surface at one or more preformed impact receiving points, wherein the contact surface is in mechanical communication with the cup, taking new abduction and anteversion readings using the gyroscopic unit to determine the relative movement of the cup caused by the tapping, and repeating this striking step and this reading step until the cup has proper abduction and anteversion readings.

In another embodiment of the present invention, the surgeon may take additional intra-operative radiographic images during this process as needed. Other embodiments may also involve taking readings from a second gyroscopic unit aligned with a point on the pelvis so that any movement of the pelvis in any direction during surgery may be detected, quantified, and corrected. Such quantified movements are then used to adjust the target abduction and anteversion angles of the acetabular cup.

In some embodiments, a sterile surgical bag may be used to enclose the gyroscopic unit(s) to allow them to be situated within the operative field.

In further embodiments, employing the use of a portal incision remote from the main incision to permit precise acetabular bone preparation and cup implantation while employing a minimally invasive surgical approach, the proper placement of the portal incision is determined using an inside-out technique by using the geometry of the acetabulum to direct a path along a trajectory extending out from the plane formed by the face of the acetabulum to a point on the skin that provides perpendicular access to the acetabulum.

To assist with proper femoral bone preparation and implantation, other embodiments may involve using a laser pointer or other positioning device to more accurately verify that the femoral broach is properly aligned with the femur while the surgeon is preparing the femur to receive the femoral prosthetic. The laser pointer may create a visible line or spot projecting generally parallel to the line of attack of the femoral broach. This permits more precise targeting of accepted anatomical landmarks such as the center of the popliteal space.

BRIEF DESCRIPTION OF THE DRAWINGS

Some elements in the drawings have been drawn not to scale so that different features can be shown with better clarity.

FIG. 2A is a perspective view of a tubular member in keeping with one embodiment of the present invention utilizing a sighting device which is directed toward the center of the acetabulum, trial cup, or attachment end of an acetabular component placement tool, as discussed below, so that the sighting device may reliably point the tubular member away from the acetabulum along a path that is generally perpendicular to the plane defined by the face of the acetabulum. The cutting member may thereby be directed through the tubular member and outward to the patient's skin where the portal incision will be made effectively at the optimal location, thereby creating access to the acetabulum along this path through the newly created portal incision.

FIG. 2B is a diagram of a tubular member in keeping with another embodiment in keeping with the present invention in which the turn radius is minimized to reduce the size of the cross-section necessary for the tubular member.

FIG. 2C is a perspective view of another embodiment of a tubular member that does not require a flexible tool.

DESCRIPTION OF THE PREFERRED EMBODIMENTS

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
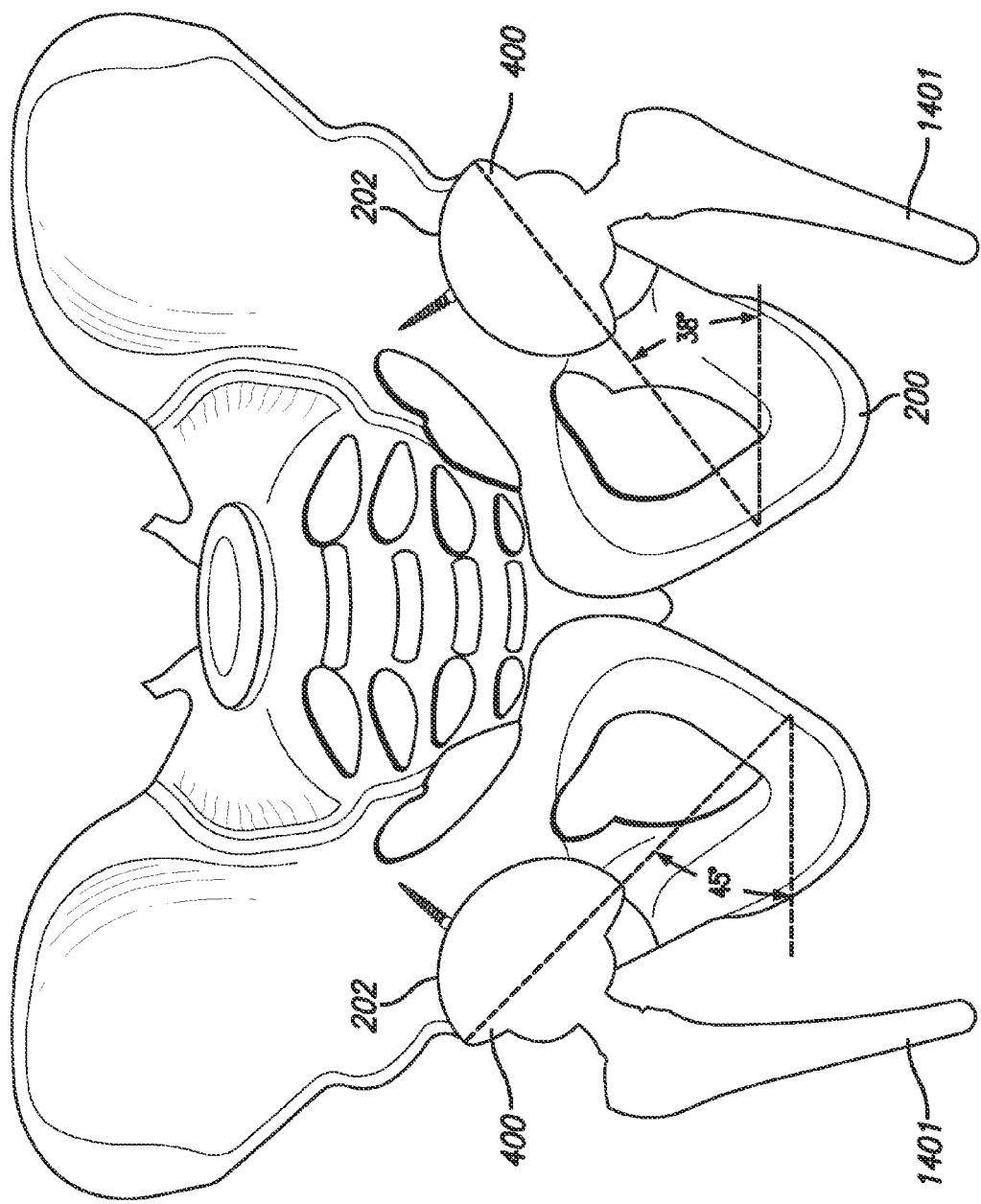
FIG. 1 is a front view of an X-ray image of the pelvis showing acetabular components on both sides of a patient in a prescribed range of abduction angles as discussed above for long-term wear and joint stability in keeping with one embodiment of the present invention.

In general, minimally invasive techniques for total hip arthroplasty require making a main incision in the hip area of the patient to access the acetabulum of the pelvis, making a portal incision (described by this author in prior disclosures) to facilitate the proper positioning of an acetabular component, properly positioning the acetabular component in the acetabulum by making adjustments of the acetabular component through the main incision and the portal incision, utilizing the main incision to facilitate preparation of the femur to receive a femoral implant, and preparing the femur with a femoral broach to receive the ball that will be coupled with the acetabular component. One major goal is to achieve the proper abduction angle and anteversion angle as shown in FIG. 1.

One embodiment of the present invention involves an intraoperative system and method of locating the optimal position for the portal incision for a minimally invasive THA, properly positioning the acetabular cup, and properly preparing the femur. The portal incision in such an embodiment, the portal incision is located by making a main incision to access an acetabulum of a patient, using either a blunt or cutting member to forge a path through the patient's tissues along a trajectory generally perpendicular to the plane defined by the face of the acetabulum, thereby identifying an appropriate portal incision location on the patient's skin while allowing the surgeon to avoid numerous blood vessels, muscles, tendons, and nerves in the process, making a portal incision at this identified point on the patient's skin. Then, the surgeon may use the direct, frontal access to the acetabulum created by this portal incision and path to prepare the acetabulum to receive an acetabular cup. This access may be further secured and maintained by using a cannula, trough or spatula device. In such instances, the surgeon may introduce the device to maintain the channel and thereby protect the contiguous tissues from additional injury by placing the device around the tip of the blunt or cutting member and then guide the trough-like device through the portal incision in into the forged path.

In some embodiments, the acetabular component or cup may then be properly positioned to greatly improve the likelihood of success and longevity of the component, including attaching the acetabular cup to the end of an acetabular component placement tool and using the acetabular component placement tool to place the cup in roughly the correct position with respect to the pelvis of the patient. Knowing the approximate position of the patient's pelvis by virtue of the use of at least a semi-secure positioning device, the surgeon may then take a first abduction and a first anteversion reading using a gyroscopic positioning unit aligned with the acetabular component placement tool. The surgeon may then use a radiography unit to take an image of the pelvis containing the newly placed cup and use this image to more accurately determine the position of the cup.

In light of this true initial position, the surgeon may then alter the position of the cup incrementally by using a striking tool to tap a contact surface at one or more preformed impact receiving points, wherein the contact surface is in mechanical communication with the cup. The surgeon may taking new abduction and anteversion readings to determine the how far the cup moved relative to the initial position due to the tapping, and then repeat the tapping and reading steps until the cup has reached a proper abduction angle and anteversion angle as indicated by the gyroscopic device display. The proper position for an acetabular cup is defined as a position in which the abduction and anteversion angles are within the predetermined acceptable ranges, as discussed above and widely researched in the literature.

This method indeed, among other benefits, allows the surgeon to properly position the cup without having to place any positioning pins in or on the patient, thereby avoiding the pain, risk of infection, and risk of pin movement that may accompany the use of positioning pin. This technique also eliminates the use of line of sight transmitters, e.g., RF type, which can be disrupted during the typical movements of personnel in and around the operative field, or by blood contacting the transmitters, or the computer crashing.

In some embodiments of the present invention, the femur may be prepared by a femoral broach mounted to a broach handle that involves a striking post and a straight-line pointer means. The means could be a light or laser pointer on an adjustable mount that is mounted on the handle to allow moving the pointer around, toward or away from, and/or along the handle or striking post. It can be locked into place once properly positioned to point along an optimal line, such as along the back of the patient's thigh generally toward or medial to the popliteal space of the knee. The surgeon then observes that the pointer continues to point at the chosen target in the direction of this chosen line while he or she repeatedly strikes the broach handle or striking post, thereby ensuring that the femoral broach itself is properly oriented and aligned with the femur.

I. Positioning the Portal Incision

In one embodiment of the present invention, the surgeon locates the optimal position for the portal incision 244 by cutting from the inside out, or from within the main incision, along a trajectory away from the acetabulum 202 perpendicular to the plane defined by the face of the acetabulum. This technique allows the surgeon to locate a safe internal starting point and a safe path directed out to the under surface of the patient's skin better avoiding certain critical structures (veins, arteries, tendons, muscle, sciatic nerve, other nerves), forging a safe path or course around these structures while "sighting" from inside or from within the main incision 242. Then, once the starting location is identified adjacent to these critical structures as observed by the surgeon through the main incision 242, a rigid, sharp or blunt or generally tubular body 100 is inserted adjacent to and without damaging these structures. The body 100 may be either curved as shown in FIGS. 2A and 2C, or angled as shown in FIG. 2B. In some embodiments, the body 100 is generally tubular and a flexible tool 108 is passed through the hollow of the body and used to cut a path in the direction of the skin 240 distal to the main incision 242 to create an acetabular portal incision 244 from the inside out. In other embodiments, the body 100 itself has a sharp or blunt front end that may be used to cut or forge a path in the direction of the skin 240 distal to the main incision 242 to create an acetabular portal incision 244 from the inside out. In both scenarios, the path may be forged adjacent to and without damaging these critical structures in a manner best achieved in this inside-out method.

That is, by contrast, existing methods generally establish a location for the acetabular portal incision from visual cues or measurement made exclusively outside of the patient's body. With such outside-in methods, however, a trajectory is created and forged in which the surgeon cannot readily observe and avoid these critical structures in order to alter the path to accommodate variations in anatomy. These methods, therefore, typically cause the surgeon to risk encountering critical blood vessels, muscles, tendons, and nerves. Severing any of these can cause serious complications and unnecessary bleeding. Indeed, most outside-in methods lend to misjudging the proper location of the portal incision due to the inaccuracies in the rotational orientation of most common external visual guides. This error in rotation can even lead to perforating the femur anteriorly or piercing the sciatic nerve posteriorly. All of this may be avoided by the several inside-out methods described herein in keeping with the present invention.

In one embodiment of the present invention, therefore, a tubular body 100 is equipped on one end with a linear sighting mechanism 104 to maintain a trajectory generally perpendicular to the plane P of the face of the acetabulum 202. As shown in FIG. 2A, in a preferred embodiment, the tubular body 100 is a hollow rod having a first portion 101 with a first opening 103, a second portion 102 adjacent to the first portion 103, the second portion 102 having a second opening 107 in communication with the first opening 103, and a bend 109 connecting the first and second portions 101, 102. In other words, the first portion 101 bends into the second portion 102.

The first portion 101 of the tubular body 100 is generally cylindrical and straight defining a first axis A and may serve as a handle. The first opening 103 may be positioned at or near the top or terminal end of the first portion 101 opposite the second portion 102. In some embodiments, the first opening 103 may be on the side surface of the first portion 101. In some embodiments, the first opening 103 of the tubular body 100 may be on an auxiliary shaft 111 protruding outwardly from the first portion 101 at an acute angle. In some embodiments, the first portion may comprise multiple openings for the surgeon to choose from.

The second portion 102 allows the tubular body 100 to be properly positioned adjacent to the acetabulum in order to identify the location of the portal incision 244. The second opening 107 defines a second axis B defining a line exiting the second orifice 107. Due to the bend 109, the first axis A and the second axis B form an acute angle from each other. In some embodiments, the angle between axis A and axis B is between 25° and 75°, in a preferred embodiment this angle is within the range of 35° and 65°. This directs any tool traveling parallel to or along the second axis to move towards the surface of the skin 240. When the tubular body is properly placed in the main incision 242.

In some embodiments, the bend 109 creates a tubular body 100 having an overall "J"-shape or hook-shape appearance as shown in FIGS. 2A and 2B. Due to the small amount of space afforded by the main incision in such surgeries, in some embodiments, the bend 109 may have a tighter curvature giving the external appearance of the tubular body more of a "T"-, "L"-, or "V"-shape as shown in FIG. 2C.

That is, preferably, the main incision should be made as small as possible. Therefore, utilizing a tubular body 100 with a "tight" bend 109, such as in the "V"-shaped embodiment in FIG. 2C, would minimize the overall lateral dimensions, or width, of the tubular body 110; thereby, allowing for a smaller main incision. With a "tight" bend, however, a flexible tool 118 may need to be particularly flexible to make the turn as easily as in a hook shaped bend. Therefore, the back wall of the bend 119 may instead have a rounded or curved shape, gradually turning away from the sighting tool 114 and up toward the second opening 117 to guide the flexible tool 118 to make the turn at the bend 119 and proceed towards the second opening 117.

The tubular body 100 may further comprise a sighting tool 104 attached to the second portion 102 in a way that it defines a line of sight or a trajectory that is parallel to the second axis B. In some embodiments, the trajectory is along the second axis B as shown in FIGS. 2A and 2B. In another embodiment, the middle of the trial cup or the middle or the backside of the attachment portion of the acetabular component placement tool may comprise a feedback mechanism to facilitate this sighting by the sighting tool 104 of the tubular body 100 and ensure that the tubular body 100 was in the correct position.

Alternatively, the sighting tool 104 could be a laser pointing device, emitting a visible laser light 106 or the like. In some embodiments, the sighting tool 104 may emit laser light 106 bidirectionally. For example, the sighting tool 104 may be a cylindrical device emitting laser light 106 from both ends in opposite directions but along the same path. One end of the sighting tool 104 could then emit a laser light 106 pointing to the middle of the acetabulum 202, the middle of the trial cup that the surgeon may use for such positioning purposes, or the backside of the attachment portion of the surgical tool 300 that attaches to the trial cup and holds it in place for such positioning purposes.

In such an embodiment, the opposite end of the sighting device 104 would then emit a laser light 106 along the trajectory to illuminate a safe path to the portal incision 244 location. Alternatively, the safe path may be illuminated by a lighting device that is fed through the hollow of the tubular body 100, such as an optical fiber or the like, and an imaging device may similarly be fed through the tubular body 100.

In some embodiments, the sighting tool 104 is configured to be removable from the tubular body 100.

Due to the hollowness of the tubular body 100, the tubular body 100 can receive a flexible tool 108 via the first opening 103 that can be fed through the first portion 101, to the second portion 102, and out the second opening 107. As the flexible tool 108 exits the second opening 107 it follows the path of the trajectory established by the sighting tool 104 parallel to or along the second axis B. The flexible tool 108 may comprise a cutting instrument 150 at one end to cut through non-critical tissues or move aside the critical tissues to create a path towards the skin 240 where the portal incision 244 is to be made. In some embodiments, the flexible tool 108 may have a blunt end.

In addition, the flexible tool 108 may be a guide wire that traverses the path established by the trajectory towards the portal incision 244 while bypassing the critical tissue. A cannula, scoopula, sleeve, spatula, or similar guide tool 120 can be passed over or along the guide wire to maintain the path access to the acetabulum and/or to put the guide tool 120 in the proper position and orientation relative to the acetabulum for performing other techniques in the surgery without damaging critical tissue. In this embodiment, a cannulated, blunt, or sharp trocar, preferably approximately 8-10 mm in diameter, or other suitable tissue-protecting sleeve can be passed over this guide wire.

The flexible tool 108 can feed through the tubular body 100 and cut through the subcutaneous tissue and simply tent the skin 240, thereby identifying the portal location 244. While the skin 240 is tented, an apex is created and a 1-1.5 cm incision is made at this apex. Alternatively, still in keeping with the present invention, the surgeon may prefer to select a feed-through cutting member that is sharp enough and rigid enough such that the cutting member itself could actually cut through the skin at this optimal incision point 244.

Figure 3:
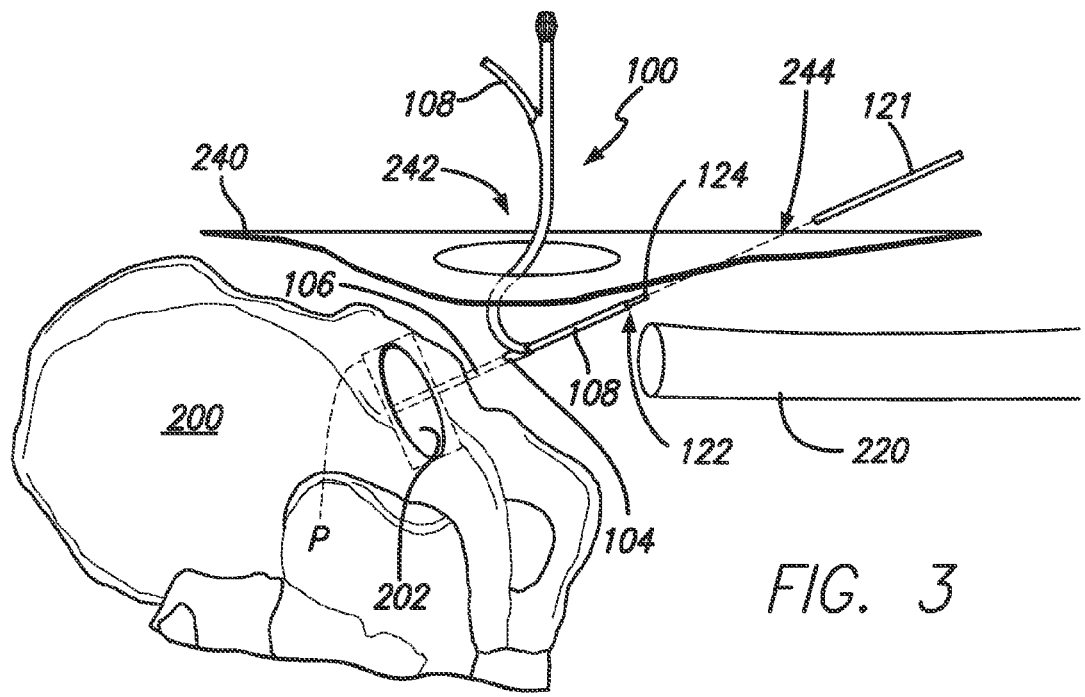
FIG. 3 is a diagram of an embodiment showing the tubular member placed through a main incision in which the sighting device assists the surgeon by pointing to the middle of the acetabulum (or trial cup, as discussed below, not shown). The cutting member thereby optimally takes a path generally perpendicular to the plane defined by the face of the acetabulum while allowing the surgeon to avoid critical blood. Note, the tissue such as nerves, tendons, ligaments, muscles, fat, and the like have been removed for clarity.
Figure 4:
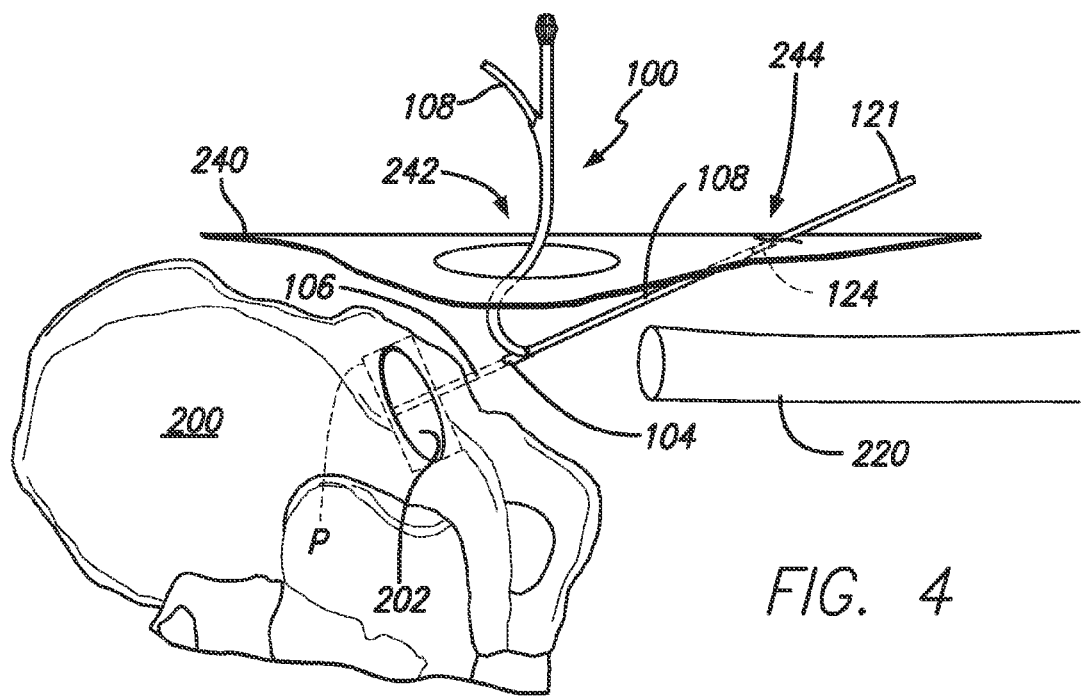
FIG. 4 is a diagram of another embodiment showing a tubular member in the vicinity of the pelvis bone and the acetabulum.
Figure 5:
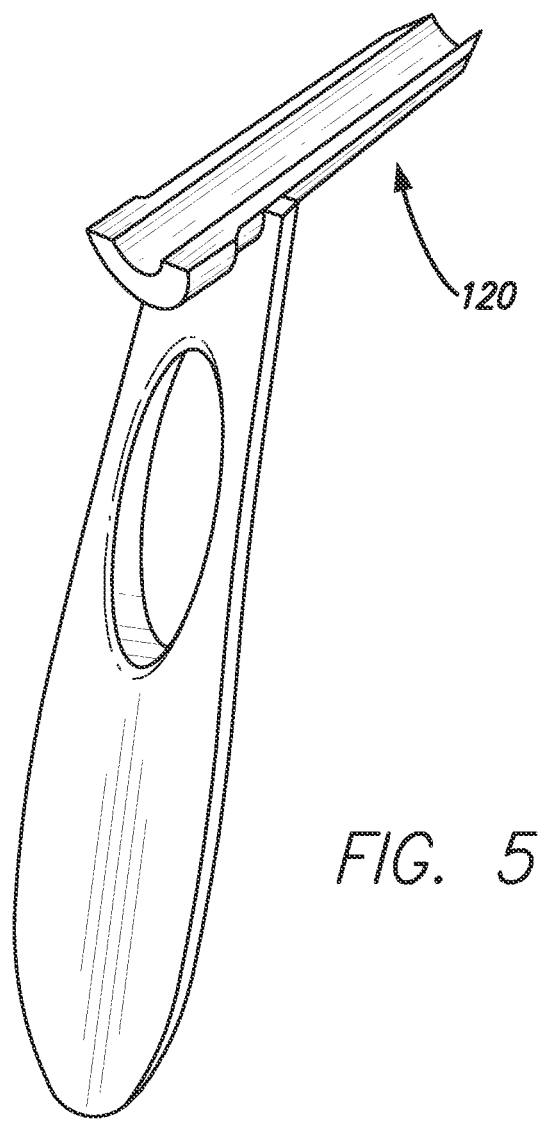
FIG. 5 is a diagram of a trough in keeping with one embodiment in which a trough is used instead of or in conjunction with a cannula.

The cutting member 150 may then be fed through the skin a short distance. This tubular body can be proportioned so that a 4-12 inch cannula 121, or a trough 120 as shown in FIGS. 3-5, can then be placed over its tip at a distance of about 1 cm (or enough to hold it in place) and the cannula 121 can then be led through the same safe soft tissue path thus avoiding veins, which in the common outside-in approach are typically severed and cause unnecessary bleeding. In such embodiments, the tip 124 or cutting member 150 of the flexible tool 108 may have a diameter that is slightly smaller than the diameter of the remainder or main body of the flexible tool 108 so that the junction where the main body transitions into the tip 124 defines a rim or ledge 122 extending radially outward from the outer surface of the tip 124, as illustrated in FIG. 3.

The flange 122 may be slight, approximately 0.5 mm, for example, and may be located about 1 inch or more or less from the free end of the tip 124. The cannula 121 can be placed over the pointed tip 124 as it penetrates the skin 240 or otherwise passes through the portal incision until the cannula or spatula reaches the ledge 122. The sharp edges of the thin metal or plastic spatula or cannula 121 will thereby be covered as it is drawn through the soft tissue pathway defined by the flexible tool 108.

In another embodiment, the working cannula can also simply be fed over a smooth trocar that is directed along the safe trajectory towards the skin. The skin is then tented, and an incision is made to permit the trocar to be accessible for mounting of and guidance of the cannula, spatula, or trough. In yet another embodiment, the flexible tool 108 may be a thin-walled cannula or tissue-protecting sleeve, such as having a wall thickness of approximately 1-3 mm, an outer diameter of approximately 8-12 mm, and a length of roughly 10-40 cm. In this way, the cannula or trough member that maintains the just created path for use in preparing the acetabulum may be introduced from the inside out.

In some embodiments, the tubular member 100 is indeed not hollow but solid instead, as illustrated in FIG. 2C, having its own pointed or blunt tip 126 that may be used to forge the path along the generally perpendicular trajectory. The second end 102 of the member 100 may then have a ledge 128 that may then receive the end of the cannula or spatula member 120 and thereby act as a cannula introducer in a similar manner as discussed above. In some embodiments, the ledge 128 of the second end 102 may taper towards the tip 126. In such an embodiment, the main body of the second end 102 may have a diameter that is slightly larger than a cannula, scoopula, spatula, sleeve, or similar type of guide tool 120 and the tip 126 may have a diameter that is smaller than any guide tool 120. This allows any guide tool 120 to slip over the end 126 and stop where the opening of the guide tool 120 is substantially the same size as the diameter of the second end 102 (i.e., at the ledge 128). In this sense, a single second end 102 can be used for different guide tools 120 having different sizes.

As mentioned above, the fixed trajectory created by the outside-in technique does not afford the surgeon with the opportunity to observe critical tissues and critical variations in anatomy or a misjudged anteversion orientation of an externally fixed sighting guide, all of which is avoided by the inside-out technique disclosed herein with reference to one embodiment of the present invention.

That is, this novel inside-out approach in this embodiment of the present invention allows the surgeon to actually see these vital structures from within and direct the potentially damaging hook or trocar through less vital tissues, such as fatty tissues, and particularly away from and around the vital structures and tissues. This visualization of the soft tissue environment can be additionally facilitated by optical fiber illumination and/or digital imaging of the environment to determine the alternative paths through the soft tissue along the trajectory generally perpendicular to the plane defined by the face of the acetabulum. In one embodiment, the illumination and imaging fibers can be passed through the cannulated hook. The fiberoptic light may also illuminate the skin from the inside out to indicate where to make the portal incision. The incision can be made on the brightest portion of the skin.

In some embodiments, the second portion 102 or 130 of the tubular body 100 or 110 may further comprise a joint or a hinge 112 or 125 to connect the first portion 101 to the second portion 102. The hinge 112 or 125 allows the sighting device 104 or 114 and the outlet portion 115 or 127 (together defining axis B) to tilt in such a way so as to change the angle between axis A and axis B. The tilt of axis B relative to axis A may be controlled by a control mechanism 113 or 129 to adjust the second portion 102 relative to the first portion 101. Preferably, the control mechanism 113 or 129 is a dial located at the top of first portion 101 or 132 of the tubular body 100 or 110 opposite the second portion 102 or 130. The control mechanism 113 or 129 may also have a locking mechanism (not shown) to lock the sighting device 104 or 114 in place once the proper angle has been established. The locking mechanism may restrict or prohibit the movement of the control mechanism 113 or 129.

In other embodiments, the surgeon may tilt the first portion 101 or 132 of the tubular member during the procedure to manipulate the blunt or cutting end through the soft tissue and create the optimal path. In such embodiments, the surgeon may be able to continuously or periodically adjust the sighting device 104 or 114 using the control mechanism to insure that the blunt or cutting end 150 continues to travel along the trajectory generally perpendicular to the face of the acetabulum.

The control mechanism 113 or 129 may utilize a connecting device (not shown), such as a flexible cable, rigid cable, rod, and the like, to operatively connect to the sighting device 104 or 114, the outlet portion 115 or 127, and/or the hinge 112 or 125. Movement of the control mechanism 113 or 129 can increase or decrease the length of the connecting device so as to cause the sighting device 104 or 114 and the outlet portion 115 or 127 to tilt. Use of the control mechanism 113 or 129 allows the surgeon to make very precise adjustments to the sighting device 104 or 114 so as to point the sighting device 104 or 114 to the center of the acetabulum 202 with minimal movement of the tubular body 100 or 110.

II. Positioning the Acetabular Component

As discussed above, proper positioning of the acetabular component 400 is critical for the prosthesis to function up to its capacity, but current methods are inaccurate, risky, and time-consuming. An acetabular component 400 may be any device designed to fit inside the acetabulum of a patient. By way of example only, an acetabular component 400 may comprise a cup, a trial cup, a reamer, a strike plate, and the like.

Figure 6:
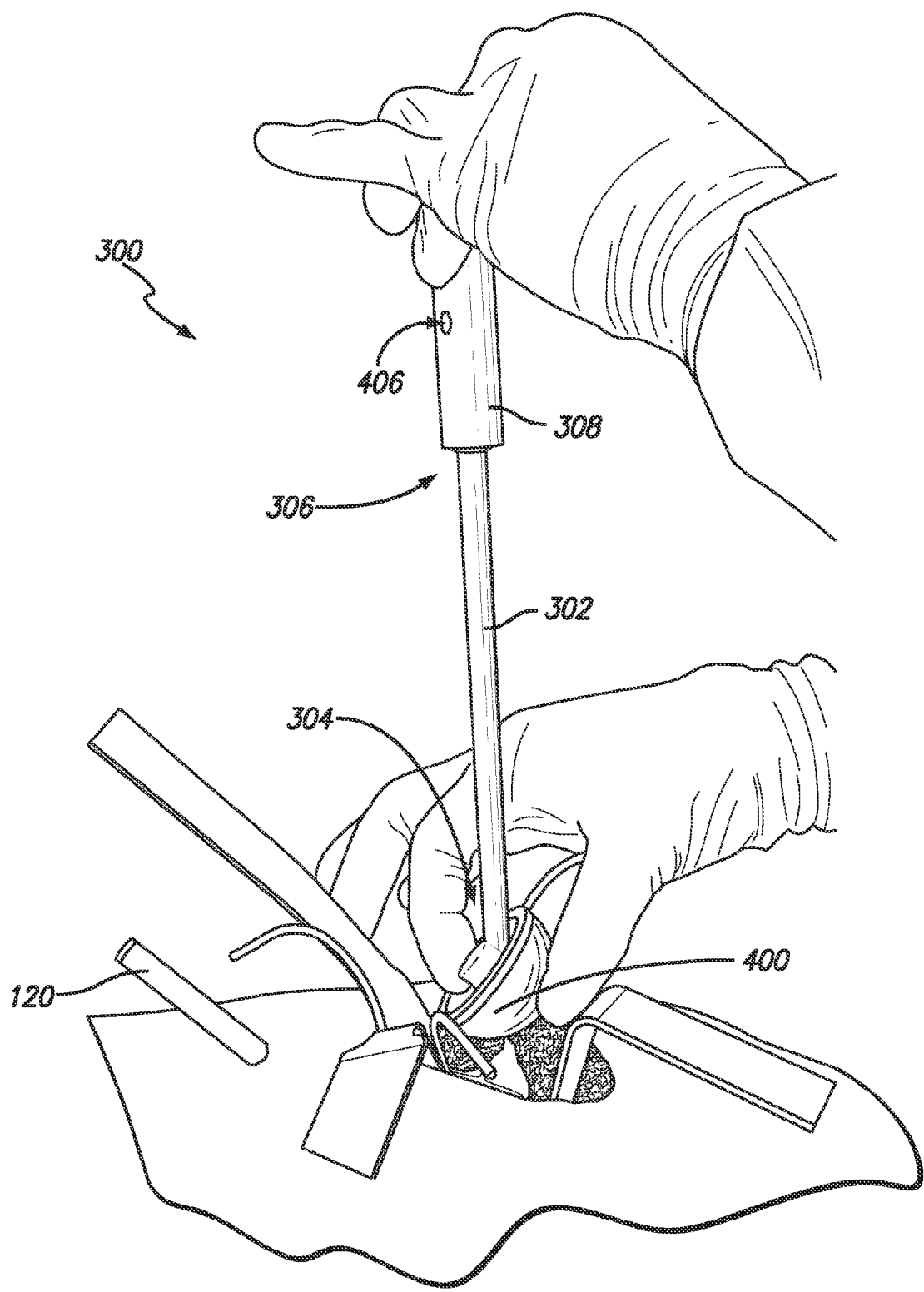
FIG. 6 is a drawing showing an acetabular component placement tool in keeping with one embodiment of the present invention inserted into the main incision with a cannula (to permit placement of, for example, an in-line impaction tool) resident in the portal incision. The side hole in the handle of the acetabular component tool is shown as round, but could readily be keyed or any other shape to ensure the proper orientation of the gyroscope holder that holds the gyroscopic unit.
Figure 7:
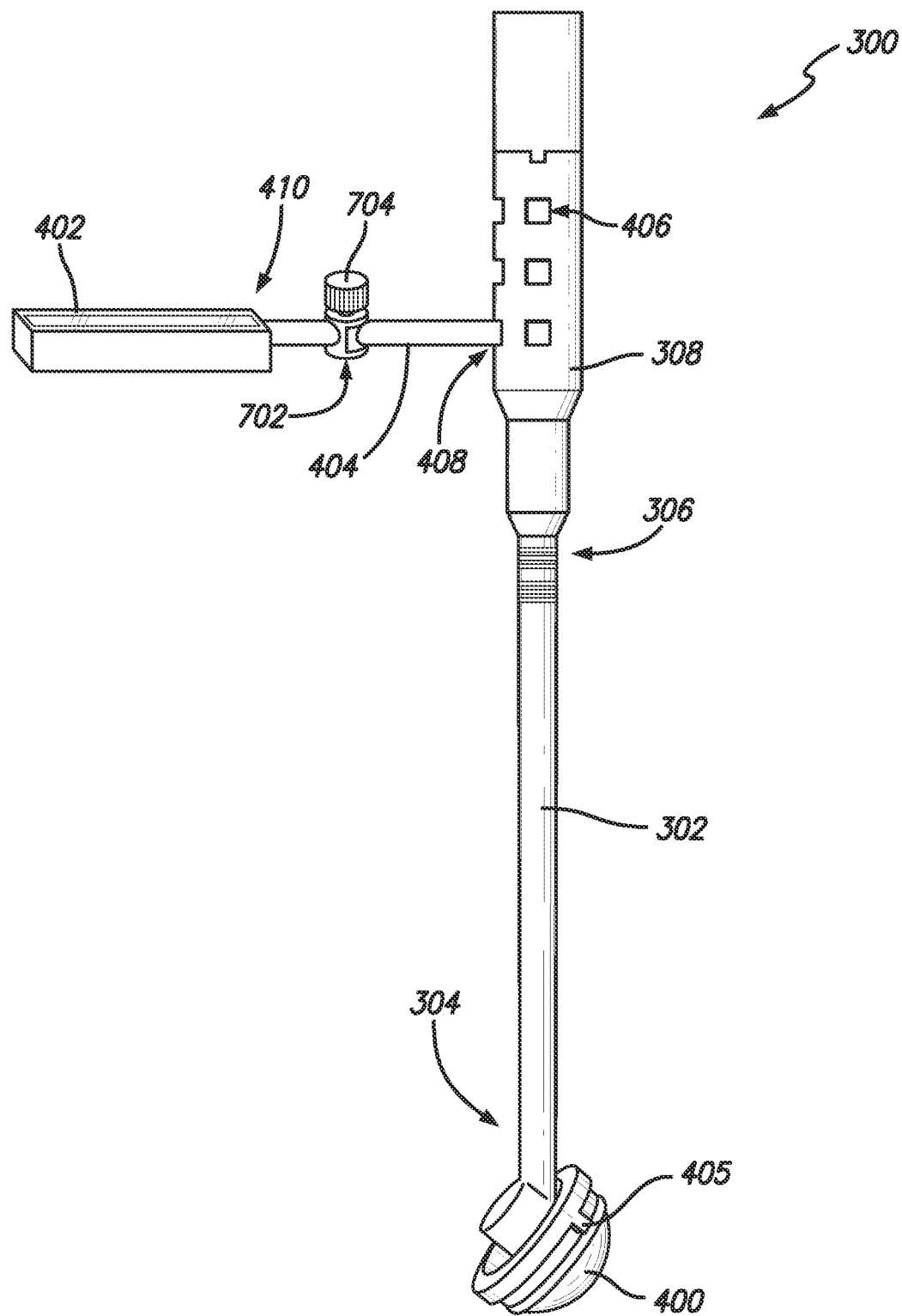
FIG. 7 is a perspective view of another acetabular component placement tool with a gyroscopic unit attached to the gyroscope holder in keeping with one embodiment of the present invention.
Figure 8:
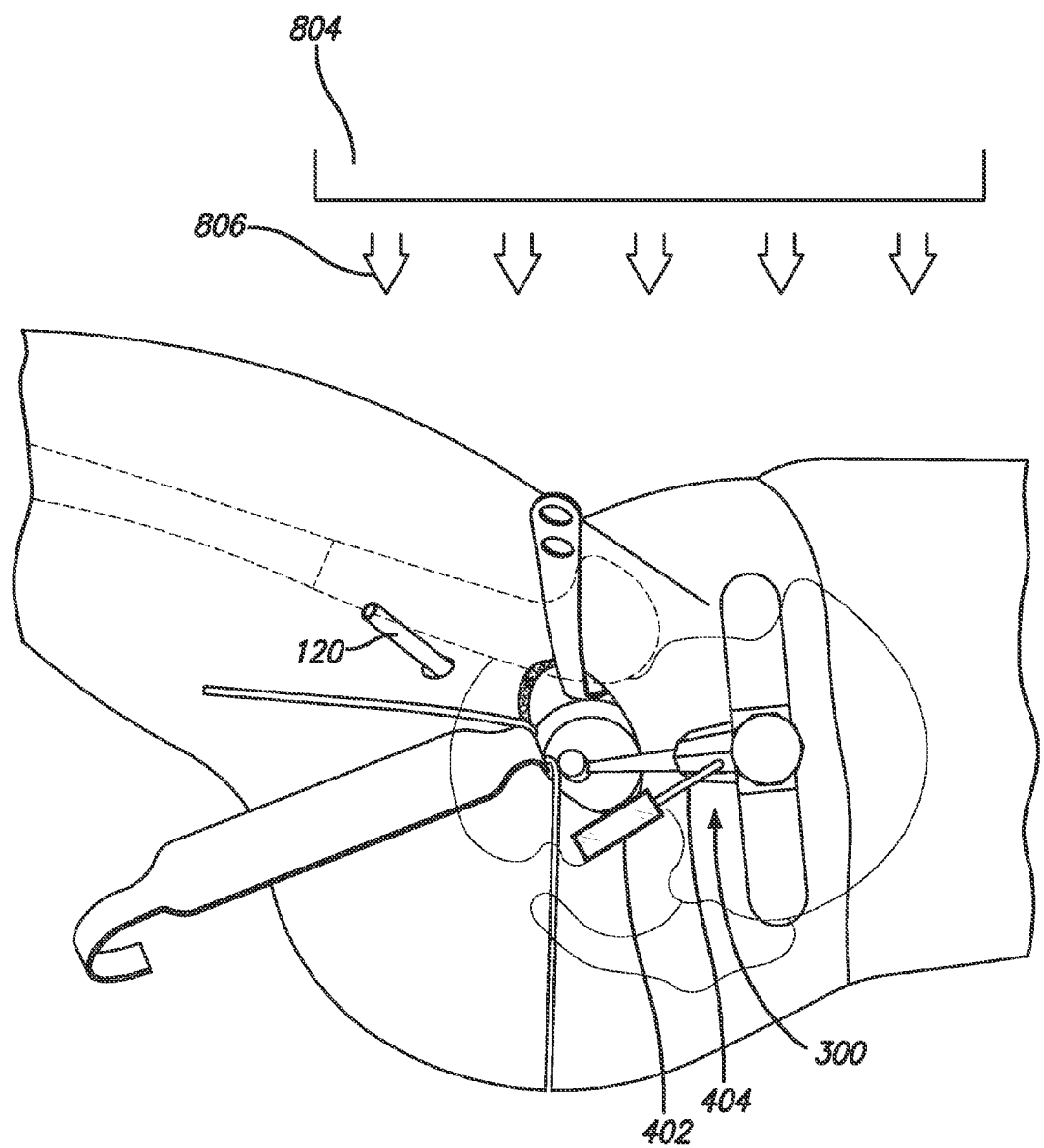
FIG. 8 is a depiction of an acetabular component placement tool in use.
Figure 9:
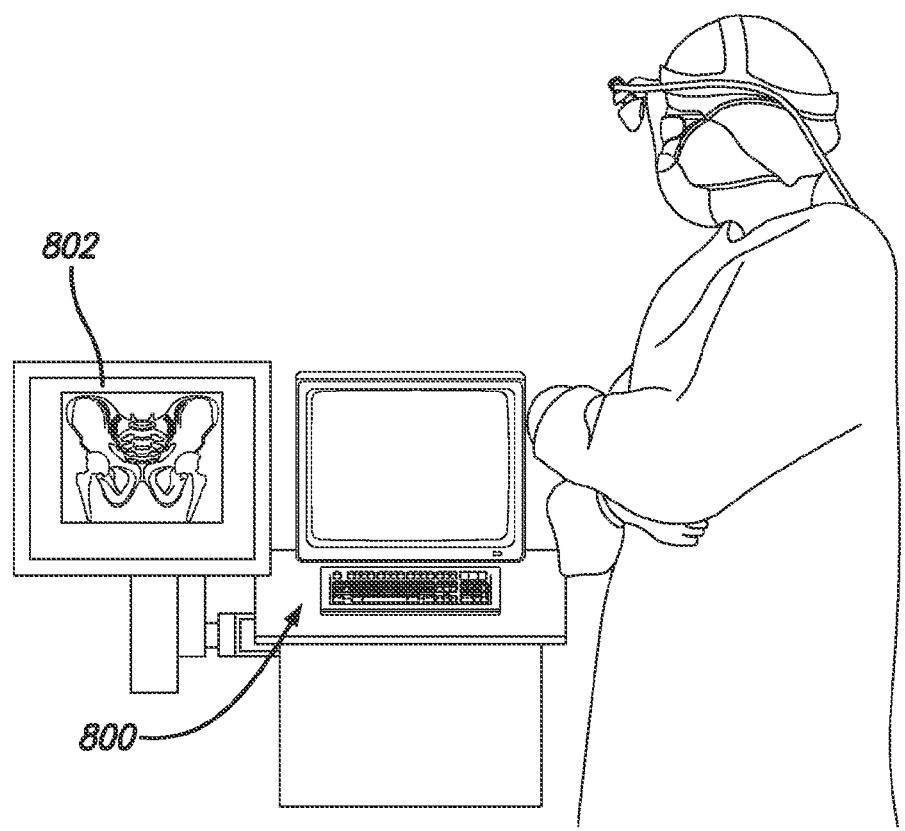
FIG. 9 is a drawing of the surgeon observing an image from a radiography unit in keeping with one embodiment of the present invention showing one preferred viewpoint of the radiography unit for use in combination with the gyroscopic unit in precisely positioning the acetabular component about two axes, the abduction angle and the anteversion angle.

In one example, an acetabular component placement tool 300, such as the standard cup holder/alignment guide shown in FIGS. 6 and 7, is commonly used in the medical profession to place and/or align the acetabular component 400 in the typical "best guess" position. Historically, because of the time consuming and technically challenging nature of obtaining an intraoperative x-ray, the true position of the component was not known until a recovery room, or office, x-ray was taken. The generally achieved success rate (achieving accurate positioning) is sixty percent (60%) (Rubash, et al.). Unless a very severe error was identified, nothing was done, and the patient carried the risk of early failure of the hip arthroplasty. If the cup position was too steep, then the plastic bearing surface could see excessive load and wear out prematurely, requiring corrective operation. If the angle was too shallow, then impingement of the femoral neck on the anterior rim of the acetabulum could result in dislocation.

Using the very recent advances in imaging technology, i.e., the availability of computer and or digital radiography, now makes it possible to obtain an accurate intraoperative image within a few seconds, such as approximately ten (10) seconds, to approximately one hundred twenty (120) seconds. This image (film or fluoroscopic image, or possibly even CT or MRI) demonstrates the result of the "first try" or "best guess" position. Thus, in one embodiment, this image of the patient's anatomy is used in conjunction with a gyroscopically enabled guide.

Having this intraoperative measurement, the surgeon now has an opportunity to make an immediate correction. At present, the sighting techniques with the traditional "best guess" instruments required one or more additional x-rays to confirm the correction. In addition, the traditional instruments were not constructed to permit careful, precise, known degrees of adjustment.

The present invention offers a new method and tool incorporating application for gyroscopic technology that provides a significant improvement when compared with the current sighting approach, i.e., sight, guess again, repeat the x-ray, and even possibly requiring that these steps be repeated again.

The present invention also eliminates significant cost, a critical factor in today's health care system. There is no pre-operative CT scan, avoiding potentially damaging radiation exposure, especially in younger patients and particularly women of childbearing age. There is no upfront cost to the hospital in the form of capital investments of up to a million dollars or more, there is virtually no disruption of the desired workflow as the required intraoperative image can be obtained in under two minutes, interpreted in less than thirty seconds, and can be acted upon immediately thereafter.

In the preferred embodiment, a gyroscopic unit 402 may be placed in a sterile holder/container and affixed to a surgical tool 302, such as a straight or carefully angled cup holder/alignment guide, as illustrated in FIG. 7. This upgrades the traditional sighting device to a metered tool providing improved estimates during initial positioning of a prosthesis. An intra-operative radiographic image of the then-present position is achieved during initial estimated placement. The radiographic measurement is then used as part of the method for achieving successful positioning or the basis for making an intra-operative adjustment. Now, upon obtaining measurements from the gyrometer and an image from the intra-operative radiographic unit, the "best guess" positioning of the acetabular component 400 relative to the acetabulum 202 can be improved, the desired positioning can be determined and quantitated as to the correction required for proper placement of the acetabular component within the acetabulum.

In order to improve the accuracy, reduce the risk, and work efficiently, besides the proper positioning of the portal incision 244, some embodiments of the present invention utilize gyroscopes removably mounted on surgical tools 302 involved in acetabular component placement, referred to as an acetabular component placement tool 300, to provide a metered approach for adjusting the acetabular component in the acetabulum. Examples of surgical tools 302 that can be used in the present invention include, but are not limited to, a trial cup holder, a cup holder/alignment guide, an impaction tool, a reamer unit, and the like.

In general, an acetabular component placement tool 300 comprises a surgical tool 302 used in positioning the acetabular component 400, and a gyrometer or gyroscopic unit 402. The surgical tool 302 has a proximal end 304 connected to a distal end 306. The proximal end 304 is the end directly attached to or directly associated with the acetabular component 400. The distal end 306 is the end that the surgeon can grasp to move the tool 302 in order to adjust the acetabular component 400. The distal or upper end 306 may comprise a handle 308 to facilitate movement of the surgical tool 302.

In the preferred embodiment, a gyroscope 402 may be attached to the distal end 306. In some embodiments, the gyroscope 402 may be attached to the handle 308. It is anticipated, based on the cost of gyroscopic technology, that only a nominal cost is required to add such a metering system, i.e., the "gyrometer," to many existing surgical instruments with only minor modifications. Indeed, in some embodiments, a single gyroscope 402 may sense and display the angular orientation of the acetabular component 400 in two or all three of the traditional three (X, Y, and Z) planes. In other embodiments, two or three separate gyroscopes 402 may be employed to sense and indicate the angular orientation of the acetabular component 400 in each of the two or three orthogonal metered planes, separately. In this way, the surgeon can feel further assured that each sensor will most accurately detect the orientation or relative orientation within the chosen metered plane (e.g., the Y plane), exclusive of any movement in either of the two other planes (i.e., the X and Z planes).

In some embodiments, the gyroscope 402 may be integrally formed with the surgical tool 302. In other embodiments, the gyroscope 402 may be removably mounted to the surgical tool 302 using a gyroscope holder 404. The gyroscope holder 404 may be an elongated rod having a first end 408 that attaches to the surgical tool 302 and a second end 410 opposite the first end 408 that attaches to the gyroscope 402. The surgical tool 302 may comprise a plurality of holes 406 at different levels. The holes 406 can be of any shape so long as the gyroscope holder 404 has a cross-sectional configuration keyed to fit into the holes 406 securely. For example, the holes 406 may be triangular, rectangular, hexagonal, star-shaped, circular with a notch, and the like. One end 408 of the gyroscope holder 404 would then have a cross-sectional shape corresponding to the shape of the hole 406 so as to fit tightly and securely into one of the holes 406 without being able to rotate. This allows the surgeon to attach a gyroscope 402 to the surgical tool 302 in such a way as to view the gyroscope readings. Adjustment of the holder, and thus the gyroscope, could also be carried out in order to facilitate a "zeroing effect," creating a true read-out rather than a relative number.

Figure 14A:
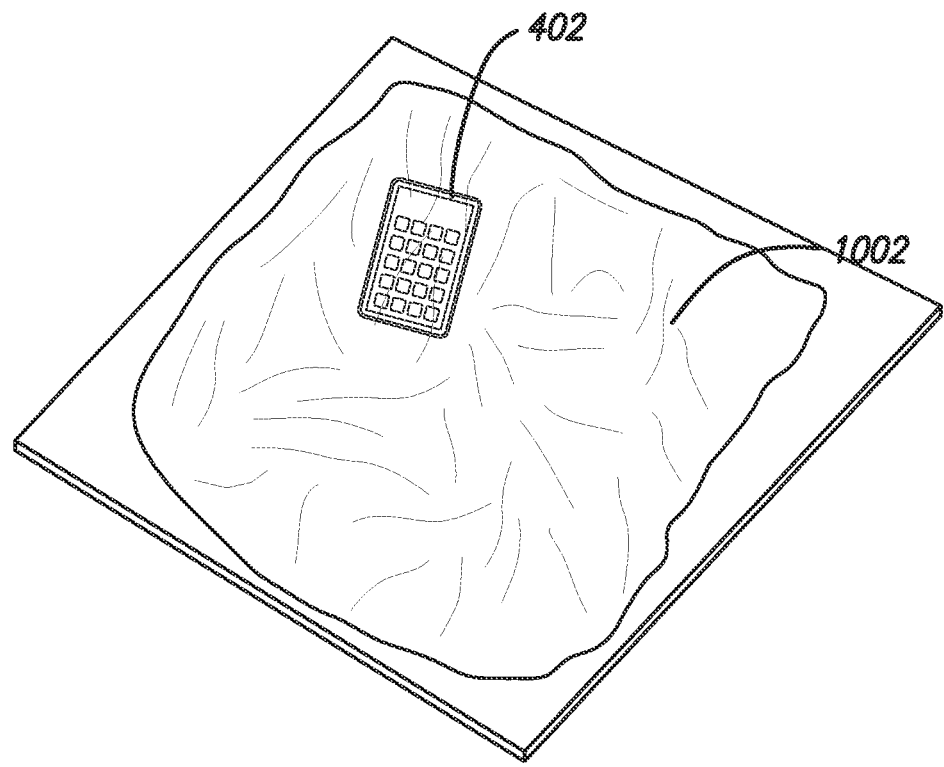
FIG. 14A is a drawing of a smartphone being used as the gyroscopic unit. It may have an open source or proprietary gyroscope application. The unit may then be placed in a sterile bag as shown for use during the surgical procedure.
Figure 14B:
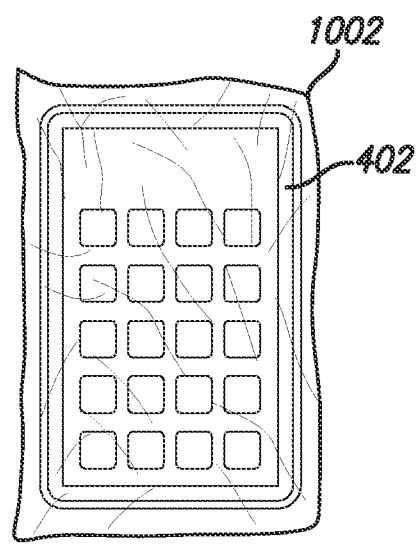
FIG. 14B is a drawing of a smartphone gyroscopic unit in the sterile bag of FIG. 10 wherein the bag is stretched tightly and any excess is folded back and away from the screen so that the screen of the smartphone (or iPod or the like) remains readily visible to the surgeon and the touch-sensitive functionality of the screen remains accessible through the bag membrane.
Figure 15:
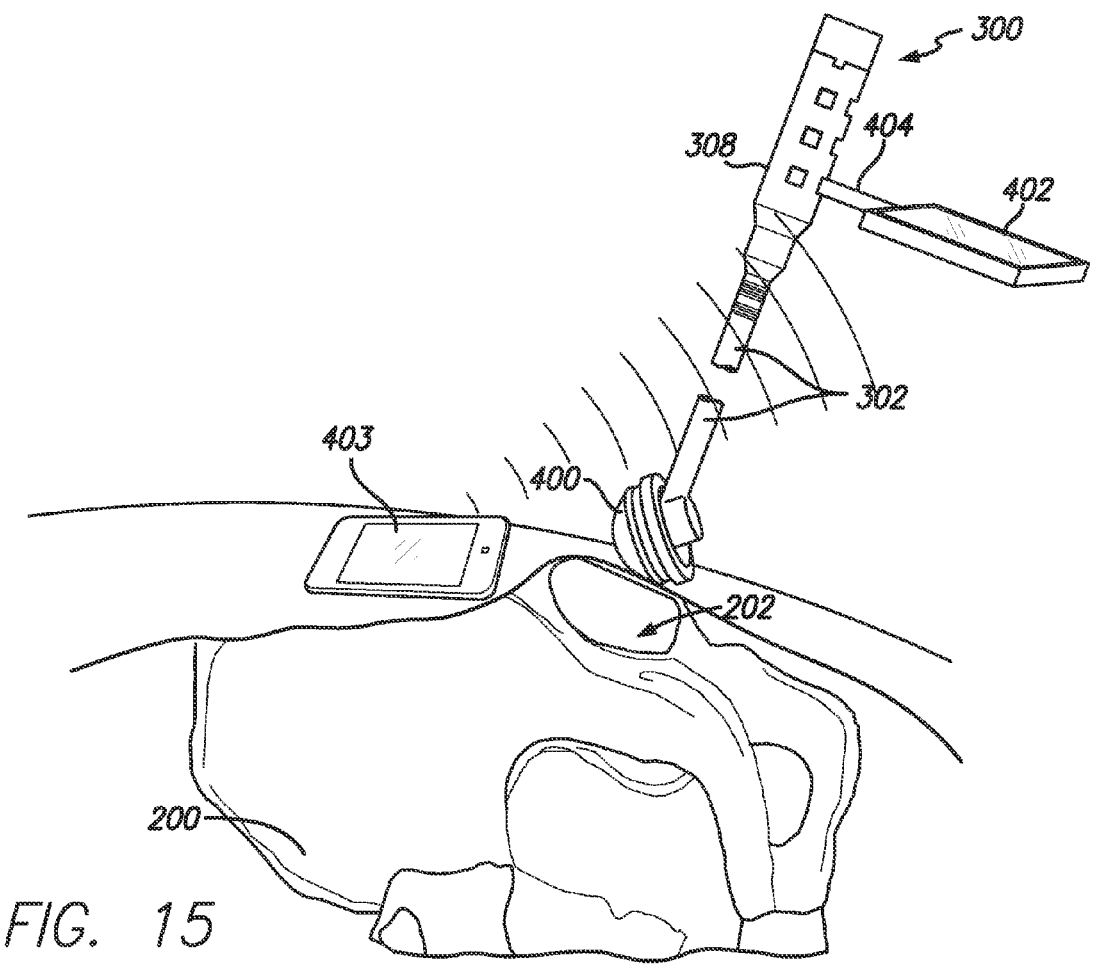
FIG. 15 is a perspective view of a second gyroscopic unit fixed to a point on the patient's pelvis.

In some embodiments, the gyroscope 402 may be incorporated in a conventional mobile electronic device 1000 containing a gyroscope 402, such as a smart phone, iPod touch, iPhone, personal digital assistant, and the like as shown in FIGS. 14A and 14B. These common mobile electronic devices can be installed with an application for converting the yaw, pitch, and tilt or roll of the gyroscope 402 into the abduction and anteversion of the acetabular component 400, and the tile of the patient's pelvis.

The gyroscopic unit 402 may be a gyrometer, inclinometer, accelerometer, magnetometer or compass, inertial sensor, GPS (Global Positioning System) unit, or an optical, infrared, or RF sensor. A gyroscope or gyrometer may be preferred in some embodiments in that such units often measure relative movement in two or three dimensions and in that many commercial devices have gyrometer units that can provide high-resolution measurements.

The gyroscope 402 can measure its relative position in three-dimensional space. Thus, any movement in the X, Y, and Z direction can be read by the gyroscope 402. When the gyroscope 402 is attached to a tool or a patient's hip or thigh, one or more reference angular readings of the tool or patient in three-dimensional space may be communicated to the surgeon by the gyroscope 402 to monitor any movement of the patient's pelvis. When associated with a smart phone or other computing device, the gyroscope 402 can display, announce, or otherwise indicate its relative position. The surgeon can set the initial position as the origin and calculate the amount of deviation from the origin necessary for correct positioning and move the surgical tool attached to the gyrometer 402 until the proper readings are reached. Alternatively, the correct positioning may be established as the origin and the gyrometer 402 may indicate the amount of deviation from the origin. Therefore, the gyrometer 402 can be moved until its readings reflect that it has reached the origin.

As mentioned above, in some embodiments, a gyroscopic unit 402 may be superior to a standard inclinometer or magnetometer. A standard inclinometer allows angular readings and correction relative to only the vertical axis. This single reading by itself cannot correctly position the acetabular component 400 to minimize wear and reduce risk of dislocation. Similarly, a magnetometer typically allows angular readings only relative to a near-linear magnetic field, such as the Earth's magnetic field. The dual-axial or tri-axial reading from the gyroscopic unit 402, by contrast, can inform the surgeon as to the relative movement of both the abduction angle (in a first plane) and the anteversion angle (in a second plane perpendicular to the first plane), as well as the tilt of the pelvis (in the third and remaining orthogonal plane).

Additional precision can be achieved if the pelvic tilt is controlled. The holder may also have a hinge 702 and set screw 704 so that the surgeon may "zero" the anteversion angle reading simply be adjusting the hinge 702 and then tightening down using the set screw 704 when the anteversion reading is just as the surgeon prefers. Examples of such hinge 702 and set screw 704 are illustrated in FIG. 7.

In the preferred embodiment, the gyroscopic unit 402 may be enclosed in a container 1002 to reduce and/or eliminate cross-contamination between the gyroscopic unit 402 and the patient. For example, the gyroscopic unit 402 may be wrapped inside a sterile bag. This also makes cleaning and reusing the gyroscopic unit 402 easy.

In yet another example that is still in keeping with some embodiments of the present invention, two or more gyroscopes 402, 403 may be used for additional reference points to compensate for movement of the patient's body, or the pelvis, rather than the movement of the acetabular component 400. For example, a second gyrometer 403 may be used as a second reference point. The second gyrometer 403 may be mounted to a point on the patient's anatomy, such as a point on the patient's pelvis 200, with a rod (not shown) or some other type of holder that would facilitate proper positioning of the acetabular component 400. In some embodiments, the second gyrometer 403 may be attached directly to the patient's anatomy without a rod, for example, with an adhesive that would still permit the surgeon to read the second gyrometer 403. The direct attachment may be removable so as to remove the second gyrometer 403 when the surgery is complete. The surgeon may then be able to verify to what degree the patient's pelvis 200 has moved since the initial readings were taken from both the first and second gyrometers 402, 403. The surgeon may then use this degree of movement of the pelvis 200 to recalibrate the first gyrometer 402 or otherwise take such adjustments into account when calculating his or her target readings on the first gyrometer 402, which, in combination with the readings from the second gyrometer 403, is reflective of the position of the acetabular component 400 in relation to the acetabulum 202 of the patient's pelvis 200. In some embodiments, first and second gyrometers 402, 403 may be in communication with each other so that the first gyrometer 402 receives the readings from the second gyrometer 403 and the first gyrometer 402 displays its readings regarding the positioning of the acetabular component 400 after compensating or adjusting for the movement of the pelvis as determined by the second gyrometer 403.

Figure 16:
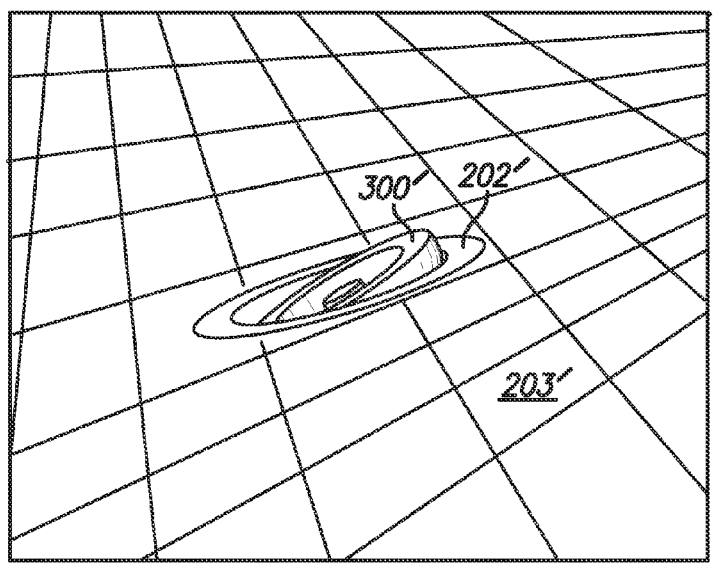
FIG. 16 is an image that may be produced by the combination of the positional data from the first and second gyroscopic units reflecting the position of the cup relative to the acetabulum and the plane defined by the face of the acetabulum during a hip replacement procedure in keeping with one embodiment of the present invention.
Figure 17:
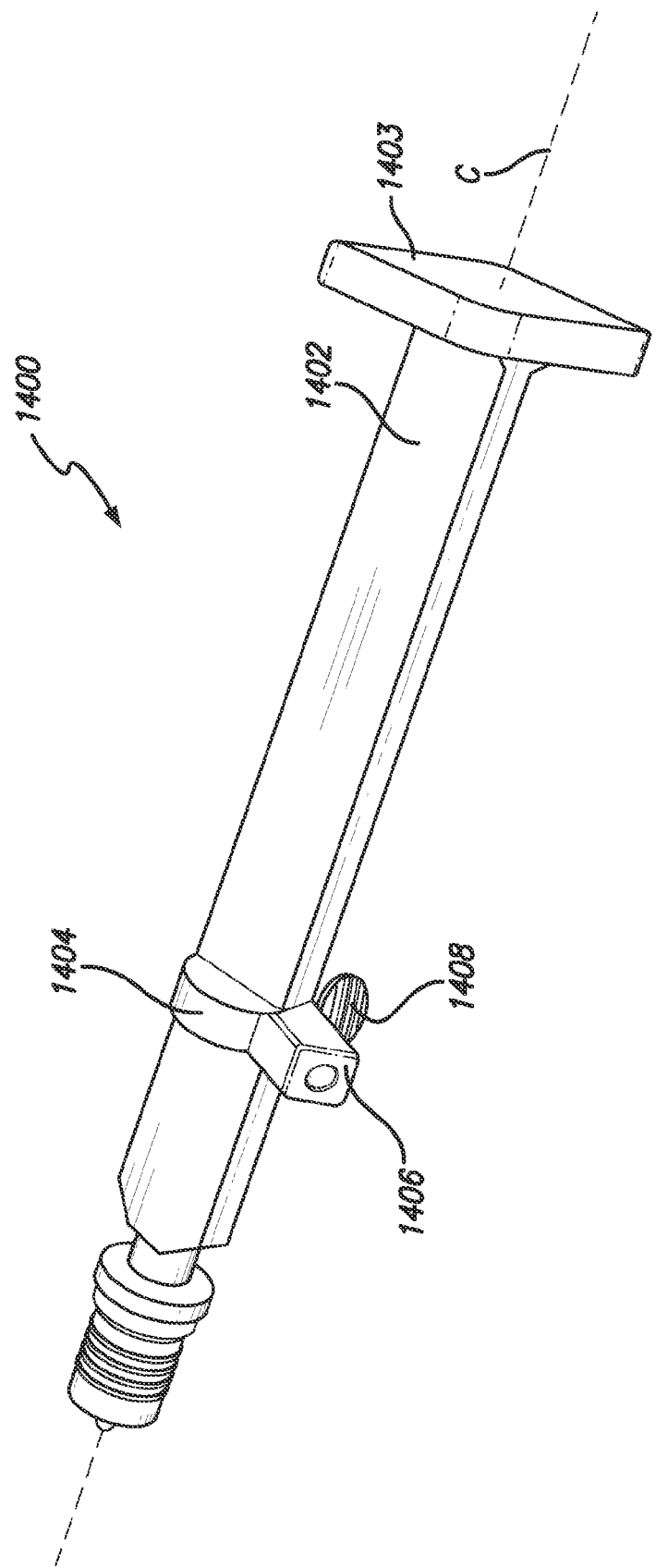
FIG. 17 is a perspective view of a femoral broach handle showing an adjustable mount for a pointer alignment device extending laterally from the handle that can allow adjustments for anteversion rotation of the broach and broach handle as it is inserted and to maintain a pointer directed precisely along the true posterior or true anterior surface of the femur. In keeping with one embodiment of the present invention, this alignment indicator—capable of indicating either or both of the broach longitudinal direction and anteversion orientation—reduces the risk of malposition of the femoral implant which can result in incorrect sizing or femur fracture.
Figure 18:
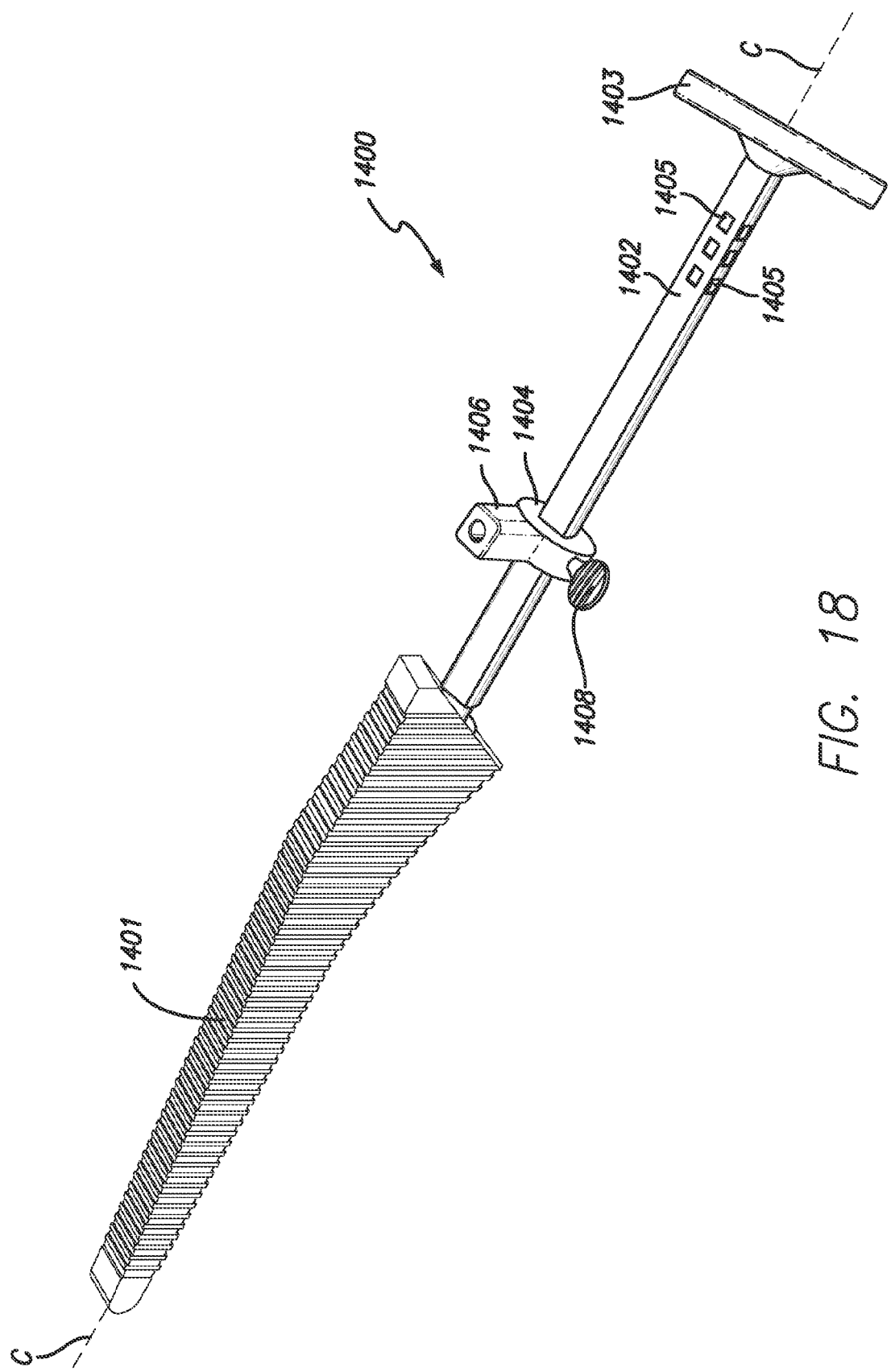
FIG. 18 is another perspective view of the femoral broach handle of FIG. 17 in combination with a broach in place in keeping with one embodiment of the present invention.
Figure 19:
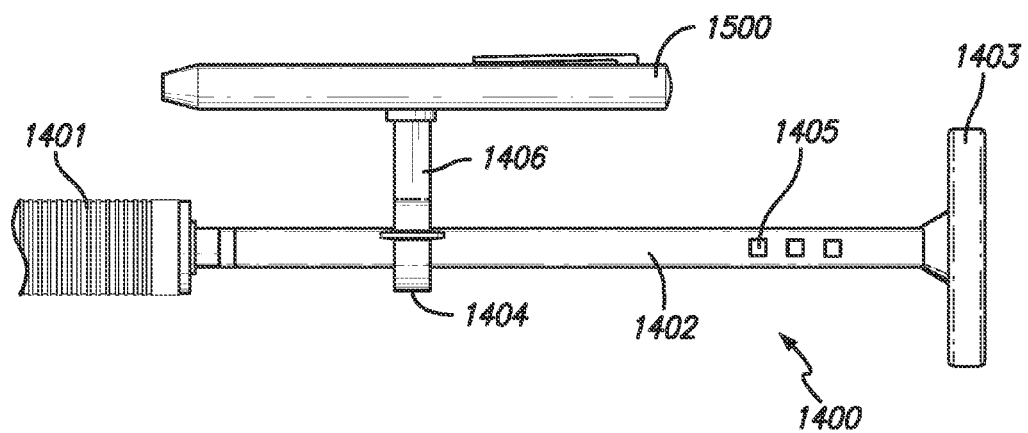
FIG. 19 is a side view of the femoral broach handle with a laser pointer device attached in keeping with one embodiment of the present invention.

In some embodiments, the two gyrometers 402, 403 may communicate with each other or with a local computer 800 so that the changes in target readings of the first gyrometer 402 (i.e., the target position of the prosthetic cup) may be tracked, communicated, and even displayed on a monitor 802 to indicate to the surgeon how the patient's pelvis may shift during the procedure. As shown in FIG. 16, computer software can transform the readings and radiographic image of the actual, relative orientation of the acetabulum 202 and acetabular component 400 into a two- or three-dimensional image representation of the cup 300'; acetabulum 202'; and plane 203' defined by the face of the acetabulum combination and display it on a screen 802 either on one of the gyrometer units 402, 403 or on the local computer 800 in real time so that the surgeon may get a good sense of how the acetabular component 400 is located and moving relative to the acetabulum 202 during the procedure as the surgeon moves the acetabular component 400 in at least two dimensions relative to the acetabulum 202 (i.e., in the abduction and in the anteversion directions) and as the patient's acetabulum 202 itself may move in any direction during the procedure.

In some embodiments, instead of, or in addition to, displaying the readings of the gyrometer 402, the gyrometer 402 may announce the readings orally, or use a tone or some other aural indicator, so that the surgeon does not have to take his eyes of the patient to read the gyrometer 402. The gyrometer 402 can announce either the current location so the surgeon knows where he needs to move the acetabular component 400, or the gyrometer 402 can announce the type of movements the surgeon needs to make the properly position the acetabular component 400.

Figure 11:
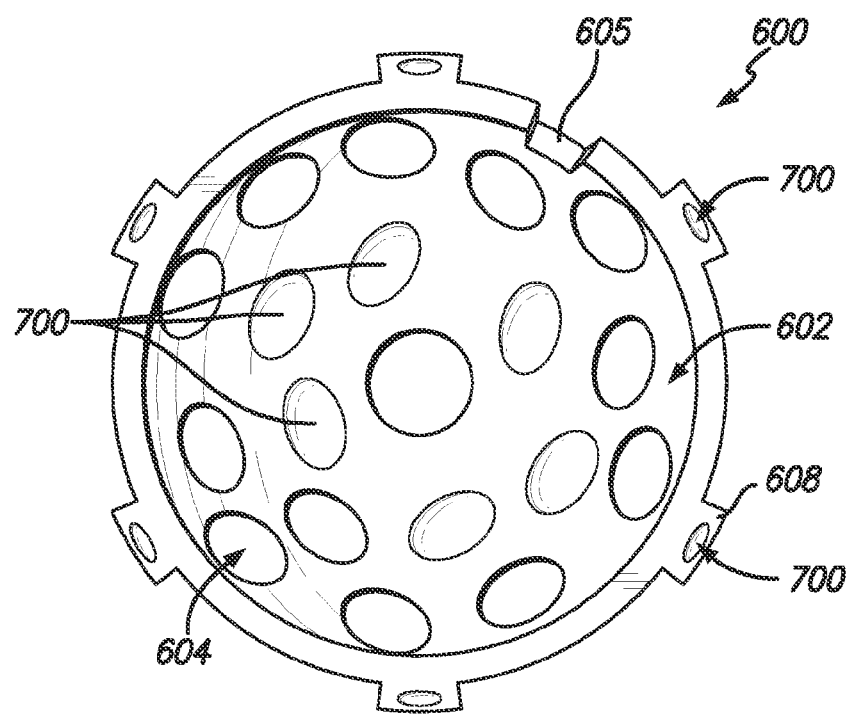
FIG. 11 is a drawing of another embodiment of the strike plate showing a number of impact points to allow the selection of the appropriate locations on the strike plate for the surgeon to tap with a tapping instrument in order to achieve the desired movement of the acetabular component in situ as it engages the bone.
Figure 10A:
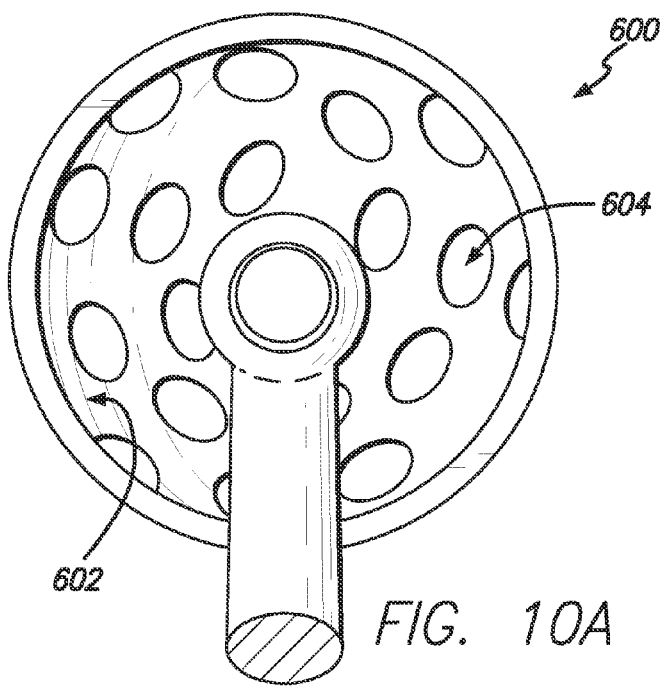
FIG. 10A is a drawing of a strike plate in keeping with one embodiment of the present invention.
Figure 10B:
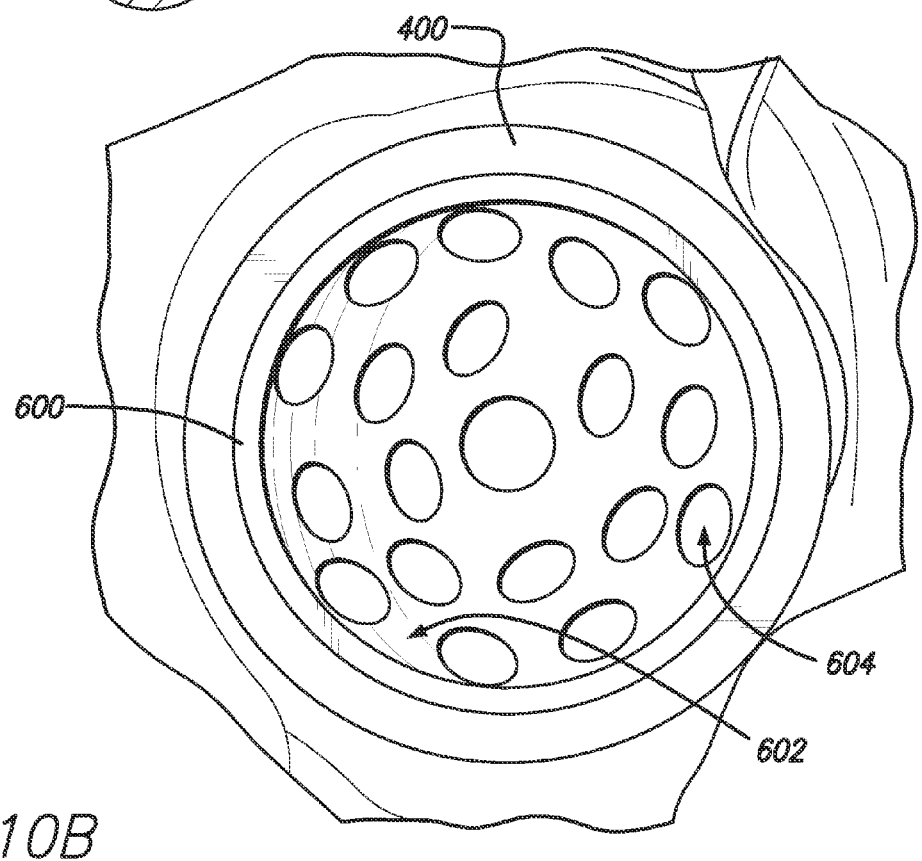
FIG. 10B is a drawing of a strike plate placed within a cavity of an acetabular component in keeping with one embodiment of the present invention.

Minor adjustments may be made with an impaction tool 600, such as a strike plate as shown in FIGS. 10A, 10B, and 11. An impaction tool 600 is configured to protect the acetabular component 400 as the acetabular component is being struck for proper positioning. In some embodiments, the impaction tool 600 may comprise multiple striking ports 700, such as corrugations, dimples, depressions, divots, recesses, and the like impaction surface on the inside 602. The outside surface (not shown) of the impaction tool 600 contacts the inside of the acetabular component 400 and creates a high-friction contact. Due to the high friction, movement of the impaction tool 600 causes movement of the acetabular component 400. Therefore, small increments of precise adjustment of the acetabular component 400 can be made by tapping on the impaction tool 600 without damaging the acetabular component 400. Such precise and incremental movements are critical, particularly because of the combination of hard and soft bone surfaces that the acetabular component 400 must engage with and seat into. The impaction tool 400 also, in some embodiments, may have regions through which the surgeon may see through to the bone to confirm that the cup is fully seated.

Figures 12A, 12B:
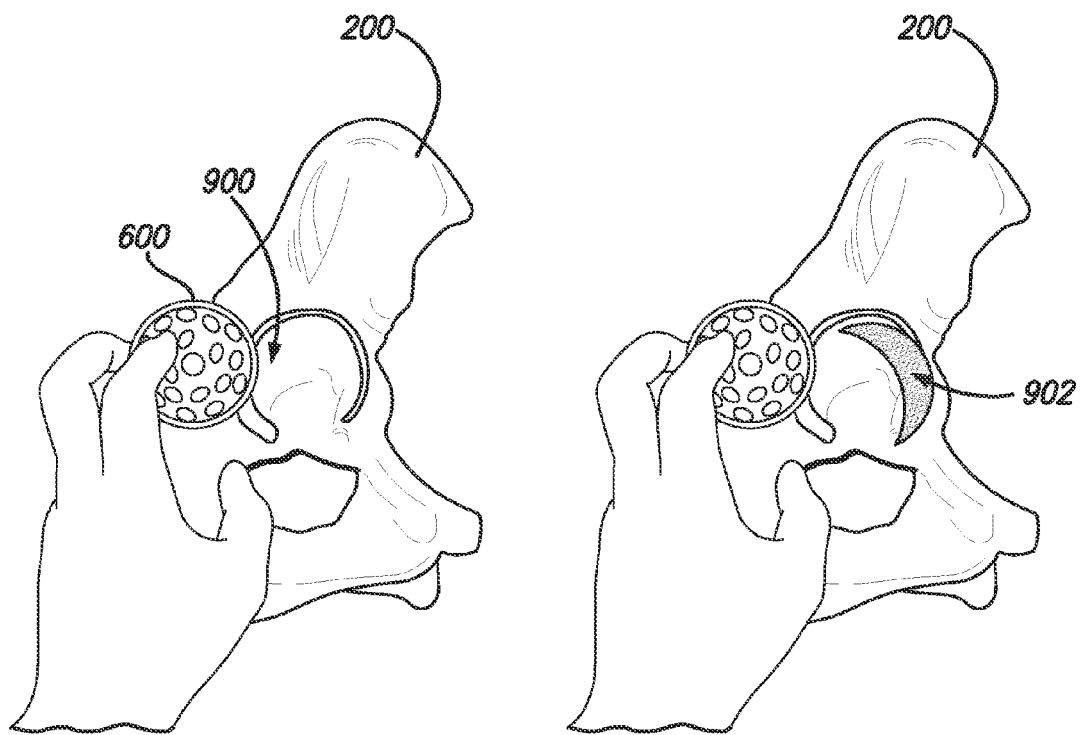
FIGS. 12A and 12B are diagrams of the relatively harder and relatively softer bone regions that the acetabular component encounters and that greatly add to the difficulty of precise placement and positioning of the acetabular component. These relatively hard and soft bone regions often cause the acetabular component to move in a complex path in reaction to the tapping described herein as part of one embodiment of the present invention. As a result, these hard and soft bone regions are one reason a strike plate having multiple impact points is particularly critical to achieving proper orientation of the acetabular component.

In some embodiments, the impaction tool 600 may be a total contact shell mating with the inner concavity of the acetabular component 400 and secured via a central screw. The exposed surface of this shell presents multiple striking ports 700 on the inner face 602 to assist with fine adjustments of abduction or anteversion as the acetabular component 400 is seated. The surgeon may alternately strike the off center ports 700 and then the central port, depending upon the changing position of the prosthesis as it is seated. It is important to appreciate that the bone density typically varies around the rim, along the walls and at the dome of the prepared acetabulum as shown in FIGS. 12A and 12B. For example, the acetabulum may have hard areas 900 and soft areas 902. Because of this variability, the prosthesis, if not monitored and controlled as it is seating, will follow the course of least resistance. Following that course creates a high risk of component malposition. Traditional positioners provide only for a central striking surface and a handle to generate a rotational force at a point removed from the implant itself and therefore not as precise as needed. The latter, central striking only technique, typically requires disengagement and re-engagement as the cup approaches final seating. This allows for the possibility of losing some pressfit as the bone is compressed with the first seating and then can lose some "stiction friction" or press fit upon reseating into the newly compressed bone.

In some embodiments, the impaction tool 600 may further comprise a flange 608 at the opening of the impaction tool 600. The flange 608 can be one continuous ring around the open edge of the impaction tool 600 parallel to and in the plane of the strike plate opening. Alternatively, the flange 608 may be short segmented flanges intermittently spaced apart around the edge of the opening. These flanges 608 can further serve as striking points to permit greater angular momentum for moving the actual acetabular component 400. In some embodiments, the flanges 608 may comprise striking ports 700, such as dimples, recesses, divots, depressions, corrugations, or other modifications to facilitate striking of the impaction tool 600. The striking elements in all cases are situated and construed in a manner that protects the surfaces of the acetabular prosthesis.

In some embodiments, the surgeon may tap the flange 608 with the impaction tool 600 while the elongated handle remains attached to the acetabular component. In other embodiments, the surgeon may remove the elongated handle so that the surgeon may have numerous other striking ports 700 to select to tap with a striking tool (not shown). In such an embodiment, the strike plate or acetabular component 400 can have a keying surface, such as one or more component keying features 605, so that the surgeon may quickly and easily re-seat the elongated handle within the acetabular component 202 from time to time to take new abduction and anteversion readings from the gyroscope 402.

For example, the component 202 may also be keyed, such as with one or more matching keying members 405, to mate with the keying surface of the impaction tool 600 in order to re-seat the proximal end 304 of the tool 300 in an identical orientation. The gyrometer holder may also be keyed in order to re-seat it in an identical orientation.

Figure 13:
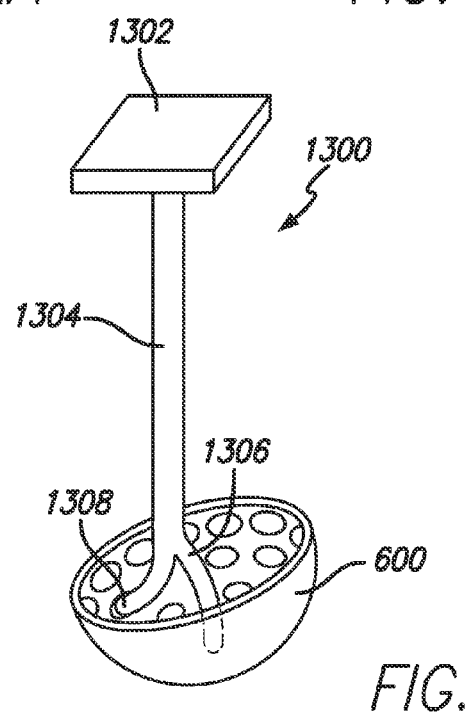
FIG. 13 is a perspective view of an embodiment of a disengagement tool to remove an impaction tool.

In some embodiments, a disengagement tool 1300 is provided for the surgeon in case the acetabular component is so firmly impacted that simply striking off center will not result in the desired repositioning and may get stuck in the hard and soft bone material 900, 902. That is, surgeons may find the cup or other component may get stuck or frozen within the acetabulum making it difficult or nearly impossible to adjust the component any further. The surgeon may then use the disengagement tool 1300 shown in FIG. 13 to carefully and minimally, in a controlled manner, pry the component, such as the impaction tool 600, loose so that he or she may then re-institute the routine described above in a further attempt to properly position the component using the radiographic unit and/or the gyroscopes.

The disengagement tool 1300 may comprises a handle 1302 and an arm 1304 attached to the handle 1302. At the end opposite the handle 1302, the arm 1304 may branch or fork into multiple prongs. The impaction tool 600 may comprise a plurality of fenestrations 604. A first prong 1306 may be configured to engage a first fenestration. A second prong 1308 may be bent at an angle relative to the arm 1304 and/or the first prong 1306 so as to engage a second fenestration. In some embodiments, the first and second prongs 1306, 1308 may be configured so that the first prong 1306 can engage the first fenestration while at the same time the second prong 1308 is able to engage a second fenestration. This can improve the leverage of the disengagement tool 1300 to more easily remove the impaction tool 600. To further improve the leverage, additional prongs may be added, one or more of the prongs may be adjustable or extendable to accommodate a number of feature configurations on the accessible surface of the impaction tool 600. In some embodiments, the disengagement tool 1300 may be configured to engage the striking ports 700 to remove the impaction tool 600.

The handle 1302 may be any shape. In some embodiments, the handle 1302 may be planar. A planar surface could provide a striking surface to controllably move or remove the impaction tool 600. In some embodiments, the handle 1302 may comprise contours so as to be ergonomically shaped to facilitate grasping of the handle 1302.

Example 1

Generally, when using an acetabular component placement tool 300, start with the "Best Guess" approach (using the traditional "Sighting" Guide approach, plus the Cup Holder/Alignment Guide), obtain a radiographic or fluoroscopic image, and then use one embodiment of the present invention to make precise adjustments.

For example, once all of the proper incisions have been made and the acetabular components 400 is initially put in place with an acetabular component placement tool 300, the present settings of abduction and anteversion are read from the gyroscopic device 402. An imaging device 804, such as those used in radiographic or fluoroscopic imaging, can be used to create a radiographic or fluoroscopic image. For example, the imaging device 804 may be an x-ray machine emitting x-rays 806. From the radiographic imaging, the degree of abduction and anteversion needed for proper placement of the acetabular component 400 can be determined. Then, as the acetabular component placement tool 300 is shifted in the desired direction(s), the gyroscopic device 400 displays the real time changes in degrees so that the surgeon knows how much movement has been made, and how much more movement in a particular direction is still required. This reading, in reference to the starting position, gives the surgeon precise affirmation that the ideal position for stability and durability has been achieved.

The application of the gyroscopic indicator offers a reading, a numerical equivalent, that records the position in space that corresponds to the instant positioning confirmed on x-ray. The correction can then be made. Precise adjustments in the two critical planes (abduction and anteversion) can now be guided by observing the gyroscopic readout. For example, the readout can be calibrated to the amount of correction desired in each plane and noted to be correct when reading zero for abduction and anteversion. Another embodiment would be to set the gyroscope at the measured abduction and anteversion and simply correct or change the component position to the desired reading which would then indicate the desired position has been achieved.

Example 2

In yet another embodiment, the best guess position can be made more precise by applying the present invention to the standard cup holder/alignment guide and, rather than relying on line of sight, i.e., identifying a neutral or zeroing orientation that at present is simply "sighted" in relation to operating room structures (a corner of the room, a vertical line of tiles on the wall, or any nearby straight vertical object) or imprecise anatomical landmarks (patient's trunk, shoulder, opposite kidney). That is to say, that the gyroscopic indicator is capable of indicating true vertical for the upright part of the guide and true zero or neutral for anteversion. After cup placement in the orientation directed by the combined references of the present invention connected (physically or remotely) to the recently redesigned alignment guide, the guide is then removed. Screws or a trial liner may then be placed. A femoral trial may also be placed in the best guess position either before or after placing the acetabular component. An x-ray or fluoroscopic image is then obtained.

Those "corrected numerical" readings are used when placing the actual acetabular component. The instrumented portion of the reamer handle can then be transferred to the standard alignment guide.

Example 3

This example is similar to Example 1 above, but including an attached "gyrometer." The reamer basket (not shown) itself can act as a surrogate for the acetabular component 400. The gyrometer 402 settings can then be noted, an x-ray taken, and any corrections identified by measuring angles on the x-ray. This could be considered a way of calibrating the gyrometer 402. When returned to the same position (as indicated by the subsequent gyrometer 402 readout), correct acetabular component 400 positioning is then achieved by placing the acetabular component 400 in position, which results in corrected gyrometer readings.

By using a digital gyroscopic unit, the surgeon can quantify the orientation in space of the acetabular component greatly improving on the "best guess" orientation in which the surgeon might otherwise eyeball the positioning. Clinical research to date (including, Rubash, et al.) confirms a 40% error rate with current "best guess" in which the surgeon does not use such digital sighting instruments.

The combination may create an advantage, including by avoiding the need for the unreliable "line of sight" relative referencing or the booting and rebooting of a computer, both of which take substantial time and have been cumbersome and unreliable. Indeed, these cumbersome and unreliable techniques have been abandoned at many centers. As stated, forty percent (40%) of the time, the position will be outside of the desired range and a correction will be desirable. The data indicates that the success rate using the intraoperative imaging and adjustment methods of the present invention can be improved from sixty percent (60%) to almost ninety-nine percent (99%)—and this significant success rate may be produced using minimally invasive surgery procedures.

Some embodiments of the present invention also may eliminate the need for reference pins in the pelvis as such pins can loosen, change position, and diminish precision. The pin sites can become infected and require treatment with costly and risky antibiotics. A persistent pin site infection could result in migration of bacteria to the new prosthesis with disastrous results. While placing pins there is risk to nearby nerves and blood vessels. Numbness, weakness, or unnecessary blood loss could occur. There is also a price to pay in terms of time and materials. Clearly, avoiding reference pins offers a significant advantage.

III. Positioning the Femoral Broach

In some embodiments of the present invention, the femur 220 is prepared by a femoral broach tool comprising a femoral broach 1401. The femoral broach 1401 may be mounted to a broach handle 1400, which comprises an elongated connecting member 1402. A striking post 1403 then may be connected either to the connecting member 1402 or directly to a portion of the femoral broach 1401 to allow the surgeon to strike the striking post repeatedly until he or she has displaced the appropriate amount of bone material from the femur to leave room for the prosthesis and any associated mounting structures and cementing material.

The lengthwise orientation of the femoral broach 1401 during this process is critical to the successful preparation of the femur 220 and ultimate positioning of the prosthesis. In previous methods, the surgeon lined up either the connecting member 1402, the striking post 1403, or the hammer itself with line of sight methods previously disclosed by Applicant in considerable detail. In short, this often entails envisioning the femoral broach 1401 to be in line with the striking post 1403 and attempting to keep the striking post 1403 therefore in line or parallel to some straight line along the patient's leg or other straight line in the operating room that serves as a proxy to the centerline of the patient's femur 220.

As shown in FIGS. 17 through 20, another aspect of the present invention is the femoral broach handle 1400 being equipped with a more precise alignment means to visibly align the femoral broach 1401 during the bone displacement. The femoral broach handle 1400 comprises an elongated connecting member 1402 defining a central axis C (which defines the line of attack), attached to a striking surface, platform, or post 1403, to hold and drive the femoral broach 1401 into the femur, and an adjustable mount 1404. The adjustable mount 1404 is connected to the connecting member 1402 in such a way as to allow the adjustable mount 1404 to rotate about the connecting member 1402 as well as slide up and down the connecting member 1402.

The adjustable mount 1404 comprises a post 1406 and a lock 1408 to receive and secure a pointing device 1500, such as a laser pointer. The post 1406 may also be telescopic to adjust the distance of the pointing device 1500 relative to the connecting member 1402. Due to the adjustable mount 1404, the laser pointer 1500 may be offset from the central axis C of the femoral broach 1401 and connecting member 1402, and it is oriented to emit a light or laser generally parallel to this central axis C. In some embodiments, the surgeon then can adjust the positioning of the pointer 1500 so that the light emitted from it runs along the back of the thigh approximately toward the popliteal space 602, strikes the back of the thigh near the region of the popliteal space 602, strikes the back of the calf just past the region of the popliteal space 602, or strikes any other desired precise reference point that guides broach and the prosthesis orientation.

The mount 1404 for the pointer 1500 may be adjustable in a number of ways relative to the connecting member 1402 to accommodate the surgical procedure. In one such embodiment, for example, the mount 1404 may be a collar rotatably mounted to the connecting member 1402, such that it can be rotated about the central axis C of the connecting member 1402. The surgeon may simply rotate the offset mounting arm about the central axis C of the connecting member 1402 and then fix the pointer at an appropriate angle using the lock 1408, such as a set screw or the like, to indicate the anteversion angle as the broach seeks the desired neutral position in the femoral canal. The mount 1404 may also be slidable along the connecting member 1402 so as to adjust the distance from the broach 1401. The mount 1404 may also have a tilting capability to allow the laser pointer 1500 to be adjusted so as to be parallel to the connecting member 1402.

In this way, the pointer 1500 may be adjusted to visibly maintain the central axis C in any preferred anteversion angle, regardless of the anteversion angle of the handle 1400 so that the surgeon can project the laser light 1600 directly over the posterior or anterior femur while orienting the broach 1401 in the same or any other desired anteversion angle. The surgeon then observes that the pointer 1500 continues to point at the chosen target in the direction of this central axis C of the connecting member 1402 as he or she repeatedly strikes the striking post 1403 or surface of the broach handle, thereby being certain that the central axis C of broach 1401 itself is properly oriented and aligned with the central axis of the femur.

Figure 20:
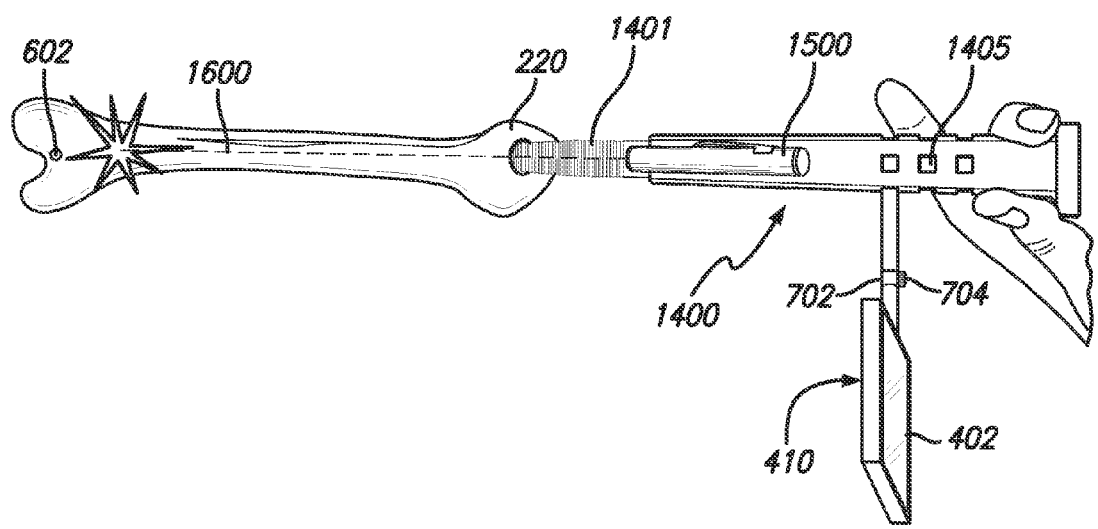
FIG. 20 is a perspective view of the femoral broach tool in use with a laser indicator light pointing toward the vicinity of the popliteal space and a gyroscopic unit to read the anteversion of the femoral broach in keeping with one embodiment of the present invention.

In one preferred embodiment, therefore, the anteversion angle of the femoral broach may be monitored, and in fact a gyroscopic unit 402 may be mounted to the broach handle 1400 in a similar fashion as discussed above with respect to the handle 1400 for the acetabular component 200. As illustrated in FIG. 20, there may be a mounting arm 404 as well as a pivot means 702 and locking means 704 so that the anteversion of the broach may be zeroed intraoperatively. Furthermore, a second gyroscopic unit 403 may be temporarily mounted to the patient's body, such as the thigh or knee region, as a reference reading to assist with a precise anteversion reading for the broach 1401 even if the patient's leg happens to move or shift during the procedure.

This is especially important when placing a cemented implant that is not guided by the prepared bone envelope. That is, the handle and alignment means may hold the femoral component in the proper longitudinal alignment while the cement sets so that any forces on the femoral component as the cement begins to set may be overcome by the surgeon. The surgeon may additionally wish to maintain a given anteversion angle for the femoral component using the same handle and alignment means.

Whether employed in the setting of the femoral prosthesis or not, the anteversion readings for the femoral broach and/or prosthesis itself can be used to calculate or modify the target anteversion range for the acetabular component 200 unique for the given patient. That is, the anteversion angle for the femoral component can fall within a wide range, ordinarily between 0° and 70°, and typically is dictated by the contours of the patient's femur. This may be due to a number of factors unique to each patient. As a general rule, therefore, the anteversion angle of the acetabular component normally is more easily varied than the anteversion angle of the femoral component.

The actual angle of anteversion of the femoral component for most patients can affect what is the appropriate target range for the anteversion angle of the acetabular component for a hip replacement to have a successful longevity. Typically, the larger the anteversion angle of the femoral component, the larger the anteversion angle needs to be for the acetabular component, leading to increasing the target acetabular anteversion angle to within a range of 20 to 25 where the patient's femoral anteversion angle is on the higher end of the above-mentioned range.

While the present invention has been described with regards to particular embodiments, it is recognized that additional variations of the present invention may be devised without departing from the inventive concept.

What is claimed is:

1. A method for locating the optimal position for a portal incision in a minimally invasive total hip arthroplasty, comprising the steps of:
    making a main incision to access an acetabulum of a patient;
    determining a trajectory generally perpendicular to a plane defined by a face of the acetabulum;
    using a cutting member to cut a path through the patient's tissue along the trajectory generally perpendicular to the plane defined by the face of the acetabulum to a point just under the patient's skin thereby allowing a surgeon to avoid numerous blood vessels, muscles, tendons, and nerves, wherein the cutting member is inserted through the main incision and used to position the trajectory generally perpendicular to the plane defined by the face of the acetabulum; and
    making a portal incision at the point to provide access to the acetabulum at a location that is along the trajectory perpendicular to the plane defined by the face of the acetabulum.

2. The method of claim 1 wherein the cutting member makes the portal incision from inside the patient's skin.

3. The method of claim 1 comprising tenting the patient's skin from the inside to locate a safe region with a circumference up to 2 inches in which to make the portal incision from the outside.

4. The method of claim 3 wherein the point is illuminated with a fiberoptic light.

5. The method of claim 1 wherein the point is illuminated with a fiberoptic light.

6. A method for locating the optimal position for a portal incision in a minimally invasive total hip arthroplasty, comprising the steps of:
   making a main incision to access an acetabulum of a patient;
   determining a trajectory generally perpendicular to a plane defined by a face of the acetabulum;
   using a cutting member to cut a path through the patient's tissue along the trajectory generally perpendicular to the plane defined by the face of the acetabulum to a point just under the patient's skin thereby allowing a surgeon to avoid numerous blood vessels, muscles, tendons, and nerves, wherein the cutting member is inserted through the main incision after determining a trajectory generally perpendicular to the plane defined by the face of the acetabulum;
   making a portal incision at the point to provide access to the acetabulum at a location that is along the trajectory perpendicular to the plane defined by the face of the acetabulum.

7. The method of claim 6 wherein the cutting member makes the portal incision from inside the patient's skin.

8. The method of claim 6 comprising tenting the patient's skin from the inside to locate a safe region with a circumference up to 2 inches in which to make the portal incision from the outside.

9. The method of claim 8 wherein the point is illuminated with a fiberoptic light.

10. The method of claim 6 wherein the point is illuminated with a fiberoptic light.

* * * * *